US008500805B2

(12) United States Patent
Kobayashi et al.

(10) Patent No.: US 8,500,805 B2
(45) Date of Patent: Aug. 6, 2013

(54) METHOD FOR MANUFACTURING APHAKIC INTRAOCULAR LENS

(75) Inventors: Atsushi Kobayashi, Seto (JP); Hiroaki Suzuki, Tajimi (JP); Ichiro Ando, Kasugai (JP)

(73) Assignee: Menicon Co., Ltd., Nagoya (JP)

( * ) Notice: Subject to any disclaimer, the term of this patent is extended or adjusted under 35 U.S.C. 154(b) by 139 days.

(21) Appl. No.: 13/142,995

(22) PCT Filed: Apr. 8, 2009

(86) PCT No.: PCT/JP2009/001631
§ 371 (c)(1),
(2), (4) Date: Jun. 30, 2011

(87) PCT Pub. No.: WO2010/079537
PCT Pub. Date: Jul. 15, 2010

(65) Prior Publication Data
US 2011/0270390 A1  Nov. 3, 2011

(30) Foreign Application Priority Data
Jan. 6, 2009 (JP) ................................. 2009-001169

(51) Int. Cl.
*A61F 2/16* (2006.01)
*G02B 5/18* (2006.01)
*G02C 7/00* (2006.01)

(52) U.S. Cl.
USPC ........... 623/6.3; 623/6.28; 359/569; 359/573; 359/576; 351/159.11; 351/159.12

(58) Field of Classification Search
None
See application file for complete search history.

(56) References Cited

U.S. PATENT DOCUMENTS

| 4,936,666 | A | 6/1990 | Futhey |
| 5,121,980 | A | 6/1992 | Cohen |
| 5,122,903 | A * | 6/1992 | Aoyama et al. ............... 359/565 |
| 5,283,690 | A * | 2/1994 | Miyake et al. ............... 359/566 |
| 6,829,093 | B1 | 12/2004 | Nakai |
| 6,873,463 | B2 * | 3/2005 | Nakai ........................... 359/574 |
| 7,188,949 | B2 | 3/2007 | Bandhauer et al. |

(Continued)

FOREIGN PATENT DOCUMENTS

| JP | U-03-035502 | 4/1991 |
| JP | A-2001-042112 | 2/2001 |
| JP | A-2008-043752 | 2/2008 |
| JP | A-2008-517731 | 5/2008 |

OTHER PUBLICATIONS

International Search Report in International Application No. PCT/JP2009/001631; dated May 12, 2009 (with English-language translation).

*Primary Examiner* — David H Willse
*Assistant Examiner* — Javier Blanco
(74) *Attorney, Agent, or Firm* — Oliff & Berridge, PLC

(57) ABSTRACT

A method of manufacturing an aphakic intraocular lens that is capable of ensuring every multi-focusing effect more securely, while reducing the impact of aperture changes and lens eccentricity. At least two reliefs whose first order diffracted lights give respective focal distances different from one another are set to overlap with each other in at least a part of an area in a radial direction of the lens, and with respect to every grating pitches of one relief having a maximum grating pitch among the reliefs set up in overlap, grating pitches of another relief are overlapped periodically in order to obtain a relief pattern, so that the resulting relief pattern is formed on a lens surface.

11 Claims, 14 Drawing Sheets

U.S. PATENT DOCUMENTS

2006/0098162 A1 5/2006 Bandhauer et al.
2007/0182924 A1 8/2007 Hong et al.
2008/0030677 A1 2/2008 Simpson

* cited by examiner

METHOD FOR MANUFACTURING APHAKIC INTRAOCULAR LENS

TECHNICAL FIELD

The present invention relates in general to an aphakic intraocular lens set in place in a lens capsule to replace the crystalline lens, and more particularly to a method of manufacturing an aphakic intraocular lens having a diffraction grating, and also an aphakic intraocular lens with a novel structure that can be favorably manufactured thereby.

BACKGROUND ART

As is well known, the crystalline lens that controls the vision sometimes lessens its adjustment function or has its characteristics such as transparency of the lens itself deteriorated due to genetic or aging factors. This consequently causes problems such as refractive disorders including myopia, hyperopia and presbyopia, or even cataract and the like, which makes it hard to obtain effective vision. To deal with such situations, an aphakic intraocular lens (hereinafter called "intraocular lens" as appropriate) has been conventionally used that is set in place in the capsule to replace the crystalline lens after enucleation and removal thereof.

However, since the intraocular lenses that have been conventionally used are monofocal ones, the problem is that the eye function ends up with no focal adjustment, although the vision is restored after the eye surgery.

To cope with such a problem, an intraocular lens capable of generating multiple foci by adopting a diffraction lens described, for example, in Patent Document 1 and the like and making use of diffraction of light is proposed. The diffraction lens described in Patent Document 1 is provided with a diffraction grating with reliefs on the lens surface and made capable of forming two foci generated by the 0th order light and first order diffracted light. Therefore, a bifocal intraocular lens is available by assigning the foci by the 0th order light and first order diffracted light for far vision and near vision respectively.

However, it is increasingly recognized in recent years that a bifocal intraocular lens that adopts a conventional diffractive lens structure is not sufficient enough to improve vision. That is, in case of an intraocular lens that adopts the diffractive lens structure described in the above Patent Document 1, for example, the 0th order light and first order diffracted light are assigned for far vision and near vision respectively, which revealed a problem that allocating energy to the mid-section between the 0th order light and first order diffracted light becomes more difficult and the contrast in the intermediate vision range gets too low.

Under these circumstances, an intraocular lens that generates multiple foci by forming multiple areas with different reliefs on the lens in its radial direction is proposed in Patent Document 2, for example, in order to make it possible to generate more number of foci. However, the intraocular lens described in Patent Document 2 had a risk of failing to achieve the desired focal effect when the diameter of incident light beam varies in cases such as pupil shrinkage. In addition, even if the design of the lens is based on a consideration of physiological pupil diameter, it is not necessarily possible to insert an intraocular lens in the desired position relative to the pupil and keep it stable therein, which poses a risk of failing to achieve the desired focal effect due to the eccentricity of the lens.
Patent Document 1: U.S. Pat. No. 5,121,980
Patent Document 2: U.S. Pat. No. 7,188,949

SUMMARY OF THE INVENTION

Problem the Invention Attempts to Solve

With the foregoing in view, it is accordingly an object of the present invention, to provide a novel method of manufacturing an aphakic intraocular lens that is capable of ensuring every multi-focusing effect more securely, while reducing the impact of pupil shrinkage and lens eccentricity.

Furthermore, this invention aims at providing an aphakic intraocular lens with a novel structure which can be favorably manufactured by the novel manufacturing method.

Means for Solving the Problem

Modes of this invention contrived to solve the above problems are described in the following paragraphs. Also, the components adopted in each modes described below are adoptable in any other possible combination.

A first mode of this invention relating to a method of manufacturing an aphakic intraocular lens provides a manufacturing method of an aphakic intraocular lens to be set in place in a lens capsule provided with a diffraction grating having reliefs extending concentrically on a lens surface, comprising the steps of: adopting various types of reliefs whose first order diffracted lights give respective focal distances different from one another for the relief pattern; setting up a synchronous structure where at least two reliefs are set to overlap with each other in at least a part of an area in a radial direction of the lens, and with respect to every grating pitches of one relief having a maximum grating pitch among the reliefs set up in overlap, grating pitches of another relief are overlapped periodically, in order to obtain the relief pattern; and forming the resulting relief pattern on the lens surface.

According to the manufacturing method of this invention, at least two foci can be generated by each first order diffracted light of at least two reliefs. With this arrangement, the 0th order light by the refractive surface of the intraocular lens, for example, is set to focus for far vision, while the first order light by one of the two reliefs is set to focus for near vision, in addition to having the other first order light set to focus for intermediate vision. This makes it possible to obtain good diffraction intensity in the intermediate vision range in addition to the far and near vision ranges, thus providing an intraocular lens capable of delivering good vision in the intermediate range. The word "relief" in this invention refers to a jagged form.

According to the intraocular lens manufactured by the present manufacturing method, various types of reliefs are set to overlap with each other. This allows the first order diffracted light to be generated by each relief in the entire area where various types of reliefs are overlapped. Therefore, unlike a diffraction lens on which different reliefs are set up in each area, as described in the above Patent Document 2 for example, it is now possible to obtain an intraocular lens more securely with an unprecedented new optical properties, whereby the desired optical properties are obtained by restricting relative variations of the diffraction intensity in a particular area caused by changes in diameter of incident light following changes in aperture and the eccentricity of the lens and the like.

Besides, especially by the present manufacturing method, a synchronous structure is set up where grating pitches of other reliefs are overlapped periodically with each grating pitch of the relief having the maximum grating pitch among the reliefs set up in overlap. That is, the synchronous structure is set up where zone radii of other reliefs are overlapped periodically with each zone radius of the relief having the maximum grating pitch. Here, the word "grating pitch" means a width of each relief between the ridge and valley lines in the radial direction. The "zone radius" refers to a radius of a ridge or valley line located on the outer side of the concentric center measured from the concentric center in the zone between the ridge and valley lines of each relief extending concentrically. Also, "concentrically" means a state of multiple streaks in forms of circles or something similar such as ovals extending in an annular pattern centered on an optical axis or an eccentric axis. Also, the "radial direction of the lens" mentioned in the claims of this invention means a radial direction centered on the optical axis, and in case the optical axis is off the geometric center of the lens, it is not necessarily identical to the radial direction of the lens relative to its outer peripheral configuration. This makes it possible to distinctly generate a peak of diffraction intensity of the first order diffracted light of each relief and to obtain a multitude of foci more certainly. In other words simply overlapping various types of reliefs cannot clearly obtain a peak of diffraction intensity of any relief and results in generating peaks of unintended order of light beams, while increasing the quantity of glare caused by stray light beams. On the contrary, according to the present manufacturing method, diffraction intensity can be allocated effectively to the first order diffracted light of other reliefs by synchronizing grating pitches of different relief patterns, thus reducing the intensity of unnecessary nth order diffracted light beams including second order diffracted light. As a result, the quantity of stray light and so forth can be lowered and the glare and the like can be reduced.

Meanwhile, the first order diffracted light in this invention is first order interference light accompanying diffraction and also is diffracted light that generates a phase difference of one wavelength. In other words, since the speed of light is slower in a medium with higher refractive index than that of air, it is the positive first order diffracted light that is the first order interference light obtained by making use of this phenomenon, and by overlapping, in delayed phases by one wavelength, the light beams that pass through reliefs adjacent to each other from the concentric center toward the periphery on a diffraction grating with reliefs having a ridge line on the center side of the concentric circle, and on the contrary, in case of using a diffraction grating with reliefs with their positive and negative reversed having a ridge line on the outer side of the concentric circle, it is the negative first order diffracted light that is the first order interference light generated on the opposite side of the reliefs obtained by overlapping, in advanced phases by one wavelength, the light beams that pass through reliefs adjacent to each other from the center toward the periphery. The "first order light" described in the claims of this invention is to be interpreted as first order light with an absolute value of both the positive first order diffracted light and negative first order diffracted light.

Also in this invention, it will suffice for various types of reliefs to be set overlapped in at least a part of the area in the radial direction of the lens, and not necessarily to be set overlapped all across the lens surface. Therefore, for example, various types of reliefs may be set overlapped only at the center of the lens or at the intermediate area in the radial direction of the lens, while only one relief may be set in other areas.

Moreover, as various types of reliefs in this invention, at least two types are good enough, and as a matter of course, three or more relief patterns can be set overlapped.

Also, the "aphakic intraocular lens" in this invention refers to an intraocular lens set in place in the lens capsule to replace the crystalline lens after the removal thereof. The shapes and materials and so forth of the reference plane where the synchronous structure of the reliefs is formed are not particularly limited. For example, such a reference plane can be an aspheric, cylindrical or tonic plane as well as a spherical plane including a convex or concave surface, or even a flat plane. Especially, in case the reference plane is other than a flat plane, optical refractive properties, in addition to the diffraction of this invention, are to be demonstrated.

A second mode of this invention related to the method of manufacturing an aphakic intraocular lens, according to the first mode, further comprising the step of setting a focal distance for a 0th order light by a refractive surface of the lens a focal distance being different from that of any of first order diffracted lights generated by the various types of reliefs.

According to the present mode, it is possible to obtain an intraocular lens with three or more foci including the focus generated by each first order diffracted light of at least two reliefs as well as the focus of the 0th order light by the refractive surface. The various types of reliefs can be formed on a refractive surface or a plane other than the refractive surface. Therefore, this mode includes an arrangement wherein a relief is formed on the non-refractive side of a lens, one side of which is a curved plane as a concave or convex refractive surface and the other is a plane as a non-refractive surface, and further includes, as a third mode of this invention related to the method of manufacturing an aphakic intraocular lens according to the second mode, an arrangement wherein the above lens surface formed with the relief pattern is the refractive surface.

A fourth mode of this invention related to the method of manufacturing an aphakic intraocular lens according to one of the first through third modes, further comprising the step of setting each relief depth of the relief having the maximum grating pitch, which is obtained by overlapping the various types of reliefs, is made constant in a zone direction.

Here, the word "relief depth" means a height of a relief in the optical axis direction at each zone radius position. According to the present mode, it is rendered unnecessary to set the depth of the relief with the maximum grating pitch for each zone, thus making it easier to set the relief pattern.

A fifth mode of this invention related to the method of manufacturing an aphakic intraocular lens according to the fourth mode, further comprises the steps of forming in each zone in the relief having the maximum grating pitch another type of relief with at least two relief depths in the area in the radial direction of the lens where the various types of reliefs set up in overlap, and setting dimensions of the at least two relief depths relative to a virtual base curve surface so as to gradually vary in the zone direction.

According to the present mode, the depth of the relief of another type can be set with more accuracy, and the peak of diffraction intensity by the relief of another type can be generated more distinctly. In this mode, the phrase "relief depths relative to the virtual base curve surface are set to gradually vary in the zone direction" includes modes where the depth gradually increases and decreases.

A sixth mode of this invention related to the method of manufacturing an aphakic intraocular lens according to the fourth mode, further comprising the steps of forming in each zone in the relief having the maximum grating pitch another type of relief with at least two relief depths in the area in the radial direction of the lens where the various types of reliefs set up in overlap, and setting dimensions of the at least two relief depths relative to the virtual base curve surface so as to be constant in the zone direction. According to the present mode, it is rendered unnecessary to set the form of another type of relief per each zone radius, thus making it easier to set the form of another type of relief.

A seventh mode of this invention related to the method of manufacturing an aphakic intraocular lens according to one of the first through sixth modes, wherein each of the various types of reliefs has a ridge line extending circumferentially with a cross-section formed with an acute vertex angle and a valley line extending circumferentially with a cross-section formed with an acute included angle.

According to the present mode, it is now possible to effectively generate diffraction effects in each of multiple reliefs and effectively generate a peak for the first order diffracted light of each type of relief.

An eighth mode of this invention related to the method of manufacturing an aphakic intraocular lens according to one of the first through seventh modes, further comprising the steps of: setting to the 0th order light by the refractive surface of the lens set a focus for far vision; setting to the first order diffracted light by one type of the relief a focus for near vision; and setting to the first order diffracted light by another type of the relief a focus for intermediate vision.

According to the present mode, it is now possible to obtain an intraocular lens having a focus for intermediate vision in addition to far vision and near vision. Therefore, the conventional problem with diffraction type lenses of lowered contrast for intermediate vision can be improved, thus making it possible to provide better intermediate vision.

A ninth mode of this invention related to the method of manufacturing an aphakic intraocular lens according to one of the first through seventh modes, further comprising the steps of: setting to the 0th order light by the refractive surface of the lens a focus for near vision; setting to the first order diffracted light by one type of the relief a focus for far vision; and setting to the first order diffracted light by another type of the relief a focus for intermediate vision.

Also in the present mode, it is now possible to obtain an intraocular lens having a focus for better intermediate vision. Here, in this mode, both near vision focus and far vision focus turn out to be the ones of the negative first order light by the corresponding relief, but as described above, the first order light in this invention is to be interpreted as first order light with an absolute value including the negative first order light.

A tenth mode of this invention related to the method of manufacturing an aphakic intraocular lens according to one of the first through ninth modes, wherein the various types of reliefs are arranged to satisfy a following equation:

$$A=(2(m-NM)+a)/N$$

where A is a zone constant of the one relief, 'a' is a zone constant of the other relief, M is a zone number of the one relief, m is a zone number of the other relief, and N is a ratio of a focal distance of the one relief relative to that of the other relief, which is expressed as:

(focal distance of the one relief)/(focal distance of the other relief).

Here, the "zone constant" means a constant for setting a zone radius of a given zone number at a certain value, and the zone radius is given by the following equation using the zone constant 'a':

$$\text{Zone radius}=\sqrt{((2m+a)\lambda f)}$$

where $\lambda$ is the design wavelength, and f is a focal distance. Also, the "zone number" refers to a number allocated for each zone in the order of 1, 2, 3, ... from the center at 0 outward in the zone direction.

According to the present mode, it is easy to set up a synchronous structure where a grating pitch of the other relief is overlapped periodically with that of the one relief.

An eleventh mode of this invention related to the method of manufacturing an aphakic intraocular lens according to one of the first through tenth modes, wherein the various types of reliefs are arranged to satisfy a following equation:

$$D \leq \lambda/(N_{lens}-N_{med})$$

where D is a dimension of the relief depth, $\lambda$ is a design wavelength, $N_{lens}$ is a refractive index of an optical material, and $N_{med}$ is a refractive index of a surrounding medium.

According to the present mode, the maximum relief depth is equal to one wavelength, which makes it possible to more securely facilitate the allocation of the 0th order light and first order light. Therefore, the present mode is preferably used in combination with other modes such as the above third mode, wherein the relief pattern is formed on the refractive surface. With this arrangement, intensity of unnecessary nth order light such as the second order light can be reduced, and the focal effects of the 0th order light and first order light can be effectively produced.

Another aspect of the present invention relates to an aphakic intraocular lens. A first mode of the invention related to the aphakic intraocular lens provides an aphakic intraocular lens adapted to be set in place in a lens capsule, and provided with a diffraction grating having a relief pattern extending concentrically on the lens surface, comprising: a synchronous structure where various types of reliefs including at least two reliefs whose first order diffracted lights give respective focal distances different from one another are set to overlap with each other in at least a part of an area in a radial direction of the lens, and with respect to every grating pitches of one relief having a maximum grating pitch among the reliefs set up in overlap, grating pitches of another relief being overlapped periodically.

According to the intraocular lens of the present mode, at least two foci can be generated by each first order diffracted light of at least two reliefs. This makes it possible to obtain a focus for far vision of the 0th order light by the refractive surface of the intraocular lens, for example, while obtaining a focus for near vision of the first order light by one of the two reliefs, in addition to obtaining a focus for intermediate vision by the other first order light. This makes it possible to obtain good diffraction intensity in the intermediate vision range in addition to the far and near vision ranges, thus providing an intraocular lens capable of delivering good vision in the intermediate range. The word "relief" in this invention refers to a jagged form.

Especially according to the intraocular lens of the present mode, the various types of reliefs are set overlapped. This allows the first order diffracted light to be generated by each relief in the entire area where various types of reliefs are overlapped, and therefore, unlike a diffraction lens on which different reliefs are set up in each area, as described in the above Patent Document 2 for example, it is now possible to restrict relative variations of the diffraction intensity in a specific area caused by changes in diameter of incident light following aperture changes and eccentricity of the lens and the like, thus enabling to obtain an intraocular lens with an unprecedented new optical properties whereby the desired optical properties are more securely obtained.

And especially in the present mode, a synchronous structure where grating pitches of other reliefs are overlapped periodically with each grating pitch of the relief having the maximum grating pitch among the reliefs set up in overlap, that is, zone radii of other reliefs are overlapped periodically with each zone radius of the relief having the maximum grating pitch. The word "concentrically" means a state of multiple streaks in forms of circles or something similar such as ovals extending in an annular pattern centered on an optical axis or an eccentric axis. Also, the "radial direction of the lens" mentioned in the claims of this invention means a radial direction centered on the optical axis, and in case the optical axis is off the geometric center of the lens, it is not necessarily identical to the radial direction of the lens relative to its outer peripheral configuration. This makes it possible to distinctly generate a peak of diffraction intensity of the first order diffracted light of each relief and to obtain a multitude of foci more certainly. In other words simply overlapping various types of reliefs cannot clearly obtain a peak of diffraction intensity of any relief and results in generating peaks of unintended order of light beams while increasing the quantity of glare caused by stray light beams. On the contrary, according to the intraocular lens in the present mode, diffraction intensity can be allocated effectively to the first order diffracted light of other reliefs by synchronizing grating pitches of different types of relief, thus reducing the intensity of unnecessary nth order diffracted light including second order diffracted light. As a result, light intensity of stray light beams and so forth can be lowered and the glare and the like can be reduced.

Also in the present mode, it will suffice for various types of reliefs to be set overlapped in at least a part of the area in the radial direction of the lens, and not necessarily to be set overlapped all across the lens surface. Therefore, for example, various types of reliefs can be set overlapped only at the center of the lens or at the intermediate area in the radial direction of the lens, while only one relief can be set in other areas.

Furthermore, as various types of reliefs in the present mode, at least two types are good enough, and as a matter of course, three or more types of reliefs can be set overlapped.

Meanwhile, the aphakic intraocular lens in the present mode means an intraocular lens set in place in the lens capsule to replace the crystalline lens after removal thereof. And the shapes and materials and so forth of the reference plane where the synchronous structure of the reliefs is formed are not particularly limited. For example, such a reference plane can be an aspheric, cylindrical or tonic plane as well as a spherical plane including a convex or concave surface, or even a flat plane. Especially, in case the reference plane is other than a flat plane, the optical refractive property, in addition to the diffraction of this invention, is to be exerted.

The second mode of this invention related to the aphakic intraocular lens according to the first mode, wherein a focal distance different from that of any first order diffracted light generated by the various types of reliefs is set for a 0th order light by the refractive surface of the lens.

According to the present mode, it is possible to obtain an intraocular lens with three or more foci including the foci generated by each first order diffracted light of at least two reliefs as well as the focus of the 0th order light by the refractive surface. In this situation, the various types of reliefs can be formed on a refractive surface or a plane other than the refractive surface. Therefore, this mode includes an mode wherein one side is a curved plane as a concave or convex refractive surface and the other a plane as a non-refractive surface where a relief is formed on the non-refractive side, and further includes, as a third mode of this invention related to an aphakic intraocular lens, an mode wherein the lens surface formed with the relief pattern is the refractive surface.

A fourth mode of this invention related to an aphakic intraocular lens according to one of the first through third modes, wherein each relief depth of the relief having the maximum grating pitch, which is obtained by overlapping the various types of reliefs, is made constant in a zone direction.

Here, the word "relief depth" means a height of a relief at each zone radius position in the optical axis direction. According to the present mode, it is rendered unnecessary to set the depth of the relief with the maximum grating pitch for each zone, thus making it easier to set the relief pattern and to manufacture the products.

A fifth mode of this invention related to an aphakic intraocular lens according to the fourth mode, wherein in each zone in the relief having the maximum grating pitch, another type of relief with at least two relief depths is formed in the area in the radial direction of the lens where the various types of reliefs set up in overlap, and dimensions of the at least two relief depths relative to a virtual base curve surface vary gradually in the zone direction.

According to the present mode, the depth of the relief of another type can be set with more accuracy, and the peak of diffraction intensity by the relief of another type can be generated more distinctly. Here, in this mode, the phrase "relief depths relative to the virtual base curve surface are set to gradually vary in the zone direction" includes modes where the depth gradually increases and decreases.

A sixth mode of this invention related to an aphakic intraocular lens according to the fourth mode, wherein in each zone in the relief having the maximum grating pitch, another type of relief with at least two relief depths is formed in the area in the radial direction of the lens where the various types of reliefs set up in overlap, and dimensions of the at least two relief depths relative to the virtual base curve surface are set constant in the zone direction. According to the present mode, it is rendered unnecessary to set the form of another type of relief per each zone radius, thus making it easier to set the form of another type of relief.

A seventh mode of this invention related to an aphakic intraocular lens according to one of the first through sixth modes, wherein each of the various types of reliefs has a ridge line extending circumferentially with a cross-section formed with an acute vertex angle and a valley line extending circumferentially with a cross-section formed with an acute included angle.

According to the present mode, it is now possible to effectively generate diffraction effects in each of various types of reliefs and effectively generate a peak for the first order diffracted light of each type of relief.

An eighth mode of this invention related to an aphakic intraocular lens according to one of the first through seventh modes, wherein the 0th order light by the refractive surface of the lens is set to a focus for far vision, the first order diffracted light by one type of the relief is set to a focus for near vision, and the first order diffracted light by another type of the relief is set to a focus for intermediate vision.

According to the present mode, it is now possible to obtain an intraocular lens having a focus for intermediate vision in addition to far vision and near vision. Therefore, the conventional problem with diffraction type lenses of lowered contrast for intermediate vision can be improved, thus making it possible to provide better intermediate vision.

A ninth mode of this invention related to an aphakic intraocular lens according to one of the first through seventh modes, wherein the 0th order light by the refractive surface of the lens is set to a focus for near vision, the first order diffracted light by one type of the relief is set to a focus for far vision, and the first order diffracted light by another type of the relief is set to a focus for intermediate vision.

Also in the present mode, it is now possible to obtain an intraocular lens having a focus for better intermediate vision. Here, in this mode, both near vision focus and far vision focus turn out to be the ones of the negative first order light by the corresponding relief, but as described above, the first order light in this invention is to be interpreted as first order light with an absolute value including the negative first order light.

A tenth mode of this invention related to an aphakic intraocular lens according to one of the first through ninth modes, wherein the various types of reliefs are arranged to satisfy a following equation:

$$A=(2(m-NM)+a)/N$$

where A is a zone constant of the one relief, 'a' is a zone constant of the other relief, M is a zone number of the one relief, m is a zone number of the other relief, and N is a ratio of a focal distance of the one relief relative to that of the other relief, which is expressed as:

(focal distance of the one relief)/(focal distance of the other relief).

Here, the "zone constant" means a constant for setting a zone radius of a given zone number at a certain value, and the zone radius is given by the following equation using the zone constant 'a':

$$\text{Zone radius} = \sqrt{((2m+a)\lambda f)}$$

where $\lambda$ is the design wavelength, and f is a focal distance. Also, the "zone number" refers to a number allocated for each zone in the order of 1, 2, 3, ... from the center at 0 outward in the zone direction.

According to the present mode, it is easy to set up a synchronous structure where a grating pitch of the other relief is overlapped periodically with that of the one relief.

An eleventh mode of this invention related to an aphakic intraocular lens according to one of the first through tenth modes, wherein the various types of reliefs are arranged to satisfy a following equation:

$$D \leq \lambda/(N_{lens}-N_{med})$$

where D is a dimension of the relief depth, $\lambda$ is a design wavelength, $N_{lens}$ is a refractive index of an optical material, and $N_{med}$ is a refractive index of a surrounding medium.

According to the present mode, the maximum relief depth is equal to one wavelength, which makes it possible to more securely facilitate the allocation of the 0th order light and first order light. Therefore, the present mode is preferably used in combination with other modes such as the above third mode, wherein relief patterns are formed on the refractive surface. This way, intensity of unnecessary nth order light such as the second order light can be reduced, and the focal effects of the 0th order light and first order light can be effectively produced.

EMBODIMENTS FOR CARRYING OUT THE INVENTION

To further illustrate this invention more specifically, its embodiments will be described in detail below referring to each figure.

Figure 1:
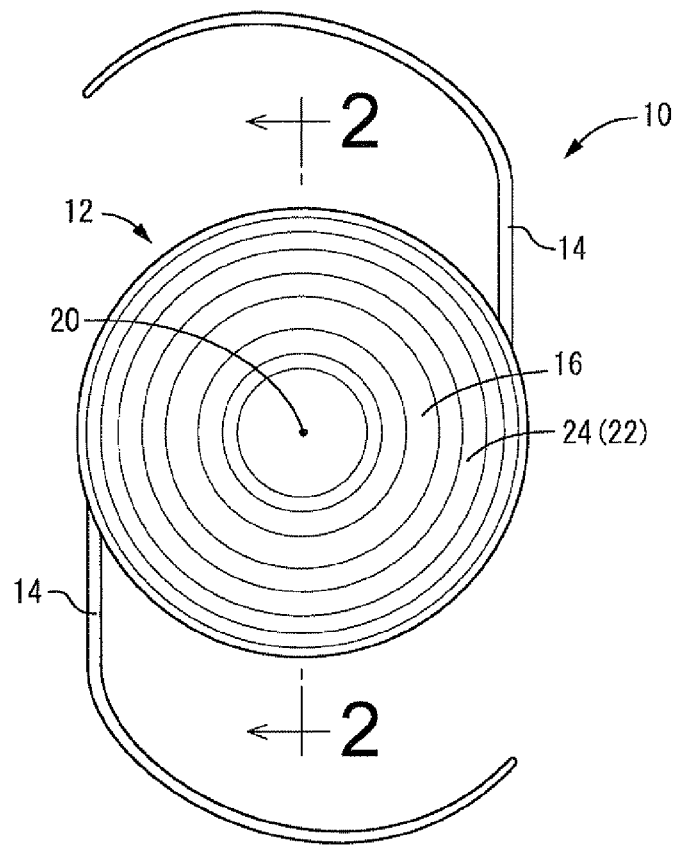
FIG. 1 is a front view diagram showing an intraocular lens as a first embodiment of the present invention.
Figure 2:
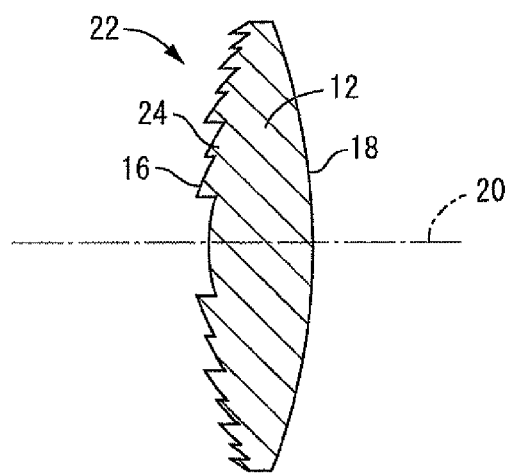
FIG. 2 is a cross-section diagram of the intraocular lens taken along line 2-2 of FIG. 1.

First of all, FIG. 1 shows a front view diagram of an intraocular lens 10 as a first embodiment related to the aphakic intraocular lens in this invention, and FIG. 2 shows a cross-section diagram of an optical part 12 of said intraocular lens 10 described later. Here in FIGS. 1 and 2, a relief pattern 24 described later is shown with its size exaggerated for better understanding.

The intraocular lens 10 comprises the optical part 12 that is part of the lens main body and gives optical properties of the intraocular lens 10 and a pair of haptics 14 that extend out from the optical part 12. The optical part 12 comprises an optical front surface 16 in an approximate convex shape of a sphere as a whole, and an optical rear surface 18 in also an approximate convex shape of a sphere as a whole. And, the optical part 12 is, in its entirety, in an approximate shape of a disc with the thicker center, and is formed as a solid of revolution formed around a geometric lens center axis 20 as a rotation axis. Meanwhile, the pair of haptics 14 are formed extending from two positions opposed in the radial direction along the periphery of the optical part 12, and each tip of the pair of haptics 14 constitutes a free end formed to curve in a direction of the lens's circumference. Such intraocular lens 10 is inserted into the lens capsule after removal of the crystalline lens and set in place to replace it by having the haptics 14 support the optical part 12 at a given position within the capsule.

The optical part 12 is provided with, as lens surfaces, the optical front surface 16 and optical rear surface 18, both made to be refractive surfaces. Also, a given focal distance is set for the 0th order light by these optical front surface 16 and optical rear surface 18.

Meanwhile, as forming materials of the optical part 12, publicly known resin materials and the like composed of various types of polymerized monomers having optical properties such as optical transparency and so forth are preferably adopted, which are exemplified more specifically by polymethylmethacrylate (PMMA) and silicone rubbers.

Also, especially on the optical front surface 16 of the present embodiment, a diffraction grating 22 is formed almost all over it. The diffraction grating 22 comprises a relief pattern 24, which has a jagged form extending continuously in the circumferential direction of the lens in a concentric way around the lens center axis 20.

Figure 3:
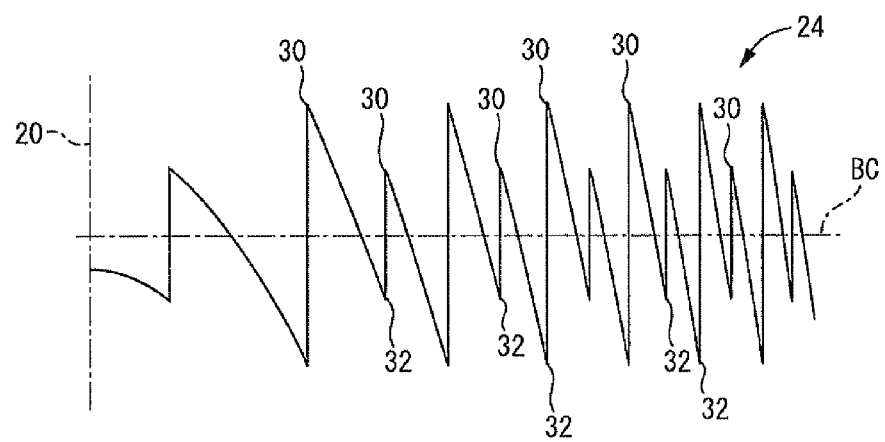
FIG. 3 is a cross-section diagram for explaining a form of a relief pattern provided on the intraocular lens shown in FIG. 1.
Figure 4:
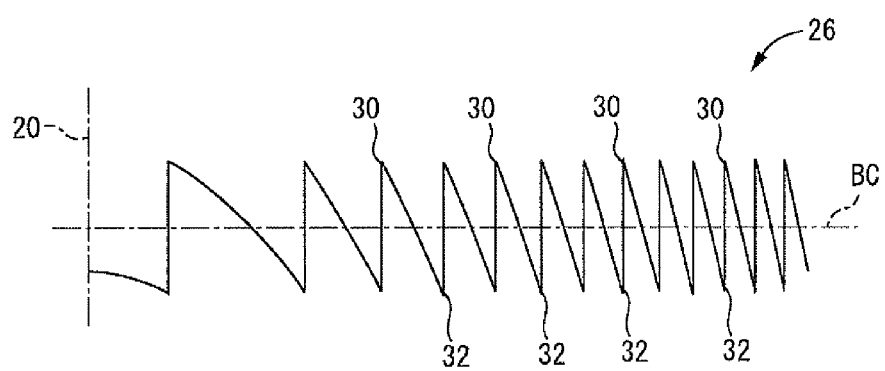
FIG. 4 is a cross-section diagram for explaining a form of a relief for near vision, which composing the relief pattern.
Figure 5:
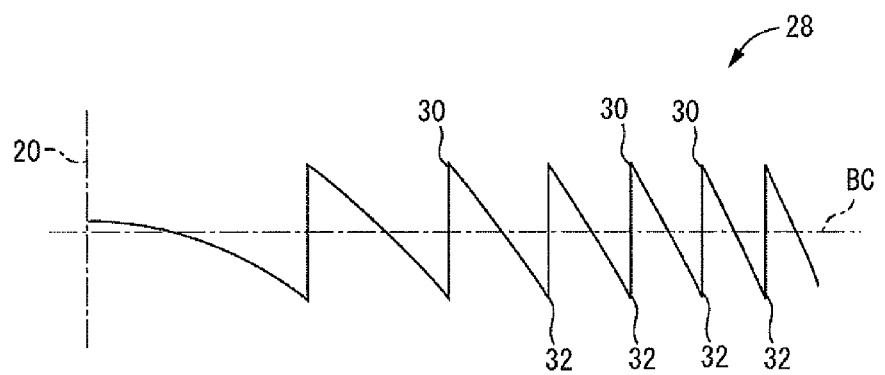
FIG. 5 is a cross-section diagram for explaining a form of a relief for intermediate vision, which composing the relief pattern.

FIG. 3 shows a cross-section diagram of the relief pattern 24 in the radial direction. Especially, the relief pattern 24 in the present embodiment is formed with an overlap of a relief 26 for near vision shown diagrammatically in FIG. 4 in cross-section in the radial direction and a relief 28 for intermediate vision shown diagrammatically in FIG. 5 in cross-section in the radial direction. These FIGS. 3 through 5 are relief profiles showing changes in height of each of the relief pattern 24 and the reliefs 26, 28, in the lens radial direction, from the base curve surface assuming that the base curve surface of the optical front surface 16 is the line BC.

These relief 26 for near vision and relief 28 for intermediate vision are each extending concentrically around the lens center axis 20, and is made in a jagged form having a ridge line 30 protruding outward (upward in FIGS. 3 through 5) from the optical part 12 and a valley line 32 protruding inward (downward in FIGS. 3 through 5) of the optical part 12.

In the following descriptions, "grating pitch" means a width between the ridge line 30 and valley line 32 in the radial direction. "Zone" means an area between the ridge line 30 and valley line 32, and a zone number is allocated for each zone in the order of 1, 2, 3 . . . from the center at 0 outward in the zone direction. Also, "zone radius" means an outer peripheral radius in each zone, that is, a radius of the ridge line 30 or valley line 32 in each zone located on the outer side of the concentric circle measured from the center of the concentric circle (lens center axis 20 in the present embodiment). Therefore, "grating pitch" is a width of each zone in the radial direction, and grating pitch of a given zone is a difference between the zone radius of said zone and the zone radius of the zone numbered one less. Also, "relief depth" is a separation distance between the ridge line 30 and valley line 32 in the optical axis direction at the zone radius position.

Especially in the present embodiment, the ridge line 30 extends circumferentially with a cross-section formed with an acute vertex angle, while the valley line 32 is formed to extend circumferentially of the optical part 12 with a cross-section with an acute included angle. These relief 26 for near vision and relief 28 for intermediate vision are each in a jagged form, wherein the ridge line 30 and valley line 32 are formed right next to each other in the lens radial direction with the valley line 32 positioned farther from the lens center axis 20, whereas the nearer side to the lens center axis 20, as opposed to the farther side, is made protruded from the optical front surface 16 in each zone.

These relief 26 for near vision and relief 28 for intermediate vision are set in such a way that each of their first order diffracted light gives a different focal distance from each other, and in the present embodiment, a refractivity of +4.00D is given to the relief 26 for near vision so as to set the first order diffracted light by the relief 26 for near vision to focus for near vision, while a refractivity of +2.00D is given to the relief 28 for intermediate vision so as to set the first order diffracted light by the relief 28 for intermediate vision to focus for intermediate vision. In addition, focal distances of the 0th order light by the optical front surface 16 and optical rear surface 18 are made different from those of the first order diffracted light of any of these relief 26 for near vision and relief 28 for intermediate vision, and the 0th order light by the optical front surface 16 and optical rear surface 18 is set to focus for far vision.

Then, the relief pattern 24 is formed by having these relief 26 for near vision and relief 28 for intermediate vision set to overlap with each other. In this situation, the grating pitch of the relief 28 for intermediate vision is made larger than that of the relief 26 for near vision, and a synchronous structure is set up where the grating pitch in each zone of the relief 26 for near vision is overlapped periodically with that in each zone of the relief 28 for intermediate vision. This allows the zone radius in each zone of the relief 26 for near vision to be overlapped periodically with that in each zone of the relief 28 for intermediate vision. Especially in the present embodiment, one of the relief depths of the relief 26 for near vision is formed in one of the zones of the relief 28 for intermediate vision, and two zones of the relief 26 for near vision are formed in one of the zones of the relief 28 for intermediate vision. In other words, each one zone of the relief 28 for intermediate vision is overlapped with two zones of the relief 26 for near vision.

In addition, these relief 26 for near vision and relief 28 for intermediate vision are set to satisfy the following equation:

$$A=(2(m-NM)+a)/N$$

where A is a zone constant of the relief 28 for intermediate vision, 'a' is a zone constant of the relief 26 for near vision, M is a zone number of the relief 28 for intermediate vision, m is a zone number of the relief 26 for near vision, and N is a ratio of the focal distance of the relief 28 for intermediate vision relative to that of the relief 26 for near vision, which is expressed as:

(Focal distance of the relief 28 for intermediate vision)/(Focal distance of the relief 26 for near vision).

This allows a synchronous structure to be set where the relief 26 for near vision and relief 28 for intermediate vision are periodically overlapped. Here, the zone constants A and 'a' are those for setting a zone radius of a certain zone number at a given value, and the zone radius is determined by the following equation using the zone constant 'a':

$$\text{Zone radius}=\sqrt{((2m+a)\lambda f)}$$

where λ is the design wavelength, and f is a focal distance.

Furthermore, these relief 26 for near vision and relief 28 for intermediate vision are each set to satisfy the following equation:

$$D \leq \lambda/(N_{lens}-N_{med})$$

where D is a dimension of the relief depth, λ is the design wavelength, $N_{lens}$ is a refractive index of the lens material, and $N_{med}$ is a refractive index of the surrounding medium. This makes it possible to more securely facilitate the allocation of the 0th order light and first order light in each of the relief 26 for near vision and relief 28 for intermediate vision. Then, the relief depth of the relief pattern 24 at the position where the relief 26 for near vision and relief 28 for intermediate vision overlap with each other turns out to be a composition of the relief depths of these reliefs 26 and 28. Moreover, especially in the present embodiment, each relief depth of the relief 28 for intermediate vision overlapped with the relief 26 for near vision is made constant in the zone direction (right-left direction in FIG. 3).

In addition, the diffraction grating 22 is formed by having the relief pattern 24 made by overlapping these relief 26 for near vision and relief 28 for intermediate vision formed on the base curve surface of the optical front surface 16.

According to the intraocular lens 10 with such a structure, the 0th order light of the optical front surface 16 and optical rear surface 18 gives a focus for far vision, while the first order diffracted light of the relief 26 for near vision gives a focus for near vision, and further, the first order diffracted light of the relief 28 for intermediate vision gives a focus for intermediate vision. This makes it possible to obtain a focus for intermediate vision in addition to far vision and near vision, thus enabling to obtain sufficient quantity of light and clearer contrast for intermediate vision.

Figure 6:
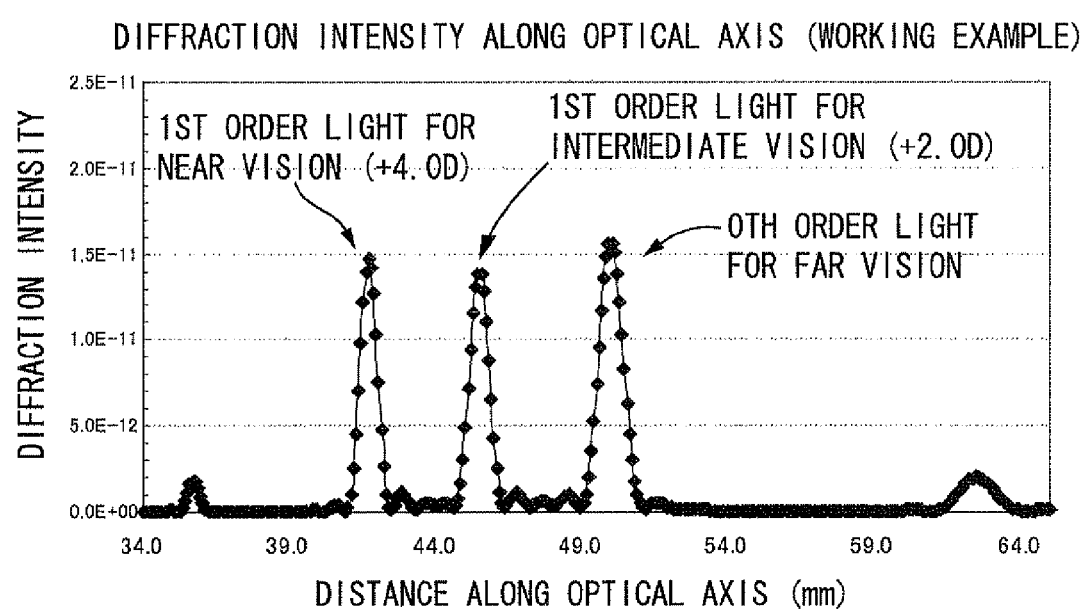
FIG. 6 is a graph showing a simulation result of diffraction intensity in the relief pattern.

Also, FIG. 6 shows a result of computer simulation of diffraction intensity along the optical axis obtained by a relief pattern according to the present embodiment. As evident from FIG. 6, according to this working example, it can be seen that a peak of diffraction intensity appears at the focus for intermediate vision of the first order diffracted light by the relief 28 for intermediate vision between the focus for far vision of the 0th order light by the optical front surface 16 and optical rear surface 18 as refractive surfaces and the focus for near vision of the first diffracted light by the relief 26 for near vision. It can also be seen that a peak is clearly generated in each of far, near and intermediate vision ranges.

Then, especially in the present embodiment, since the relief pattern 24 is formed by an overlap of the relief 26 for near vision and relief 28 for intermediate vision, each first order diffracted light is formed in the entire range of the relief pattern 24. This makes it possible to restrict relative variations of the diffraction intensity in a particular area caused by changes in diameter of incident light following pupil shrinkage and eccentricity of the optical part 12 and the like, thus enabling to obtain the desired optical properties more securely.

Additionally, especially in the relief pattern 24 of the present embodiment, the relief 26 for near vision and relief 28 for intermediate vision are formed in a synchronous structure where their grating pitches overlap periodically with each other. This makes it possible to clearly obtain a peak of each first order diffracted light of the relief 26 for near vision and relief 28 of intermediate vision, thus decreasing the quantity of light such as stray light and reducing the glare and the like.

Figure 7:
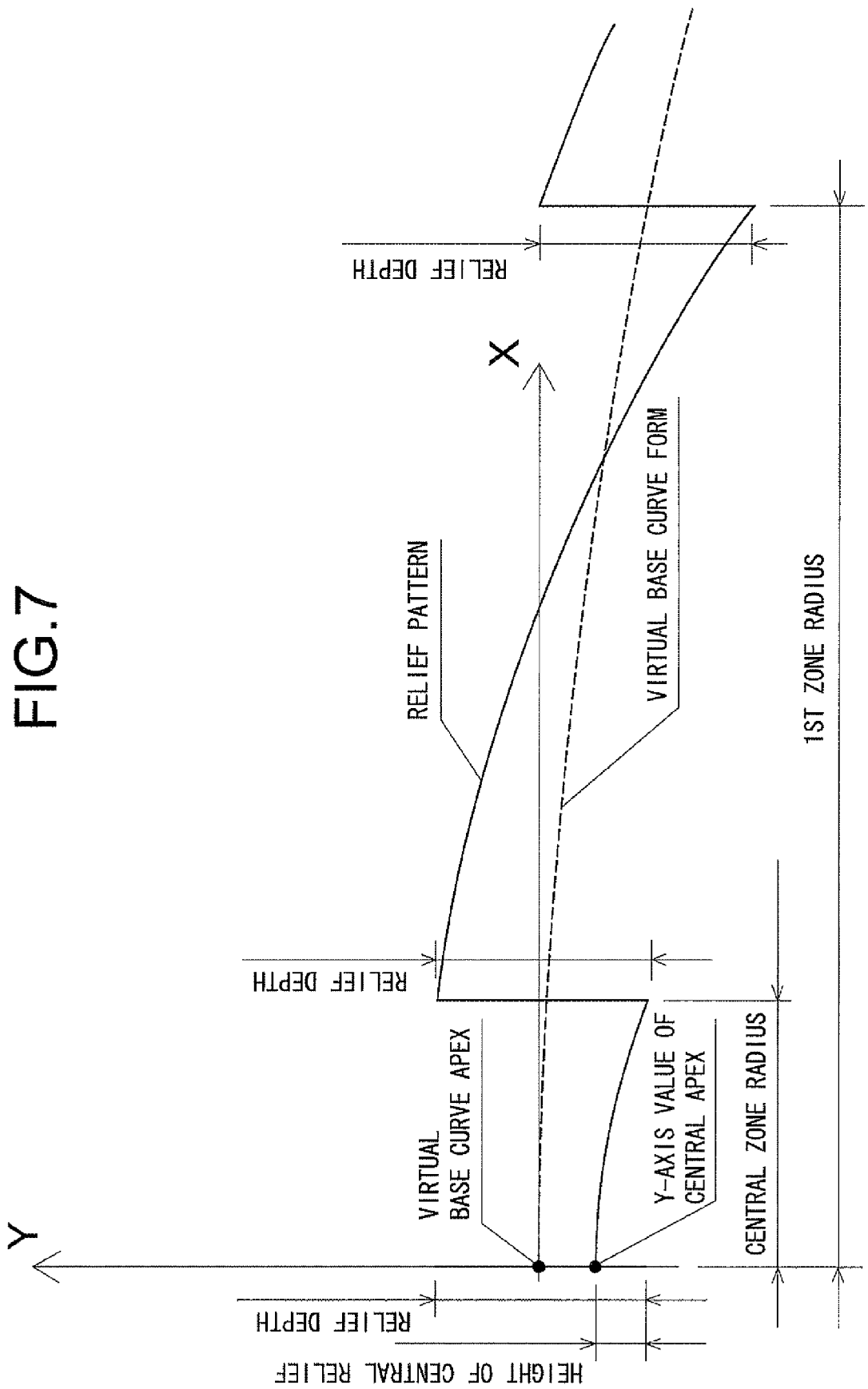
FIG. 7 is a diagram for explaining a design method of the relief pattern.

Next, a method of manufacturing an aphakic intraocular lens that can be favorably used in manufacturing the intraocular lens 10 such as the one mentioned above will be described below in reference to FIG. 7.

First of all, forms of the optical front surface 16 and optical rear surface 18 where the 0th order light generates a focus for far vision are designed as refractive surfaces. In this situation, the focal distance of the 0th order light by the optical front surface 16 and optical rear surface 18 is set at a distance different from the focal distance of the first order light of either the relief 26 for near vision or relief 28 for intermediate vision. A conventionally known method can be adopted, as appropriate, in the design of such optical front surface 16 and optical rear surface 18.

Next, the form of the relief 26 for near vision with the dioptric power at +4.00D is designed. The relief depth is generally determined by the following equation:

$$\text{Relief depth} = p/(n_{lens} - n_{med}) \quad (1)$$

where p is a phase difference, $n_{lens}$ is a refractive index of the lens material, and $n_{med}$ is a refractive index of the surrounding medium.

Here, the relief depth is desirably a phase difference of no more than one wavelength considering the allocation to the 0th order light that generates far vision, and more preferably, is equal to or smaller than a phase difference of half the wavelength. Then, assuming that λ is the design wavelength and, for example, $p=\lambda/3$, $n_{lens}=1.500$, $n_{med}=1.336$, λ=500 nm, the following value is obtained:

$$\text{Relief depth} = (0.0005/3)/(1.500 - 1.336)$$
$$= 0.001016260163\ldots$$

Next, the zone radius of the central zone (zone number=0) is determined upon consideration of the pupil diameter and zone pitch. For example, the central zone is set small enough at 0.2 mm compared to the pupil diameter. A diffraction formula with the central zone diameter set at any value is given by modifying the following equation;

$$\text{Zone radius} = \sqrt{2m\lambda f} \quad (2)$$

into the following equation;

$$\text{Zone radius} = \sqrt{((2m+a)\lambda f)} \quad (3)$$

where m is a zone number, λ is the design wavelength, f is a focal distance (f=1,000/power), and 'a' is a zone constant.

Therefore, assuming that the central zone radius is 0.2 mm, the zone constant 'a' can be determined by the following equation;

$$0.2 = \sqrt{((2\times 0+a)0.0005\times 250)}$$

and therefore a=0.32, and consequently, the equation to calculate the zone radius with the central zone radius set at 0.2 mm is given as follows:

$$\text{Zone radius} = \sqrt{((2m+0.32)\lambda f)} \quad (4)$$

As evident from the equation (3), an increment of the zone constant 'a' by 2 corresponds to an increment of the zone number by one. Therefore, the height of the central relief is determined as follows:

$$\text{Height of central relief} = \text{relief depth} \times (a/2)$$
$$= 0.0001626016261\ldots$$

Besides, since the midpoint of the relief depth is where it intersects with the virtual base curve, the Y-axis value of the central apex is determined as follows on a coordinate system with its origin at the base curve apex:

Y-axis value of central apex = height of central relief −

(relief depth/2)

= 0.0001626016261 −

(0.001016260163 /2)

= −0.0003455284554 ...

TABLE 1

Relief for near vision

| Zone No. | Curvature radius of virtual base curve | Zone origin (X-axis) | Zone terminal (X-axis) | Curvature center of Zone (Y-axis) | Zone curvature radius |
|---|---|---|---|---|---|
| 0 | 14.384 | 0.0000000 | 0.2000000 | −12.8785710 | 12.8782254 |
| 1 | 14.384 | 0.2000000 | 0.5385165 | −12.8791445 | 12.8798150 |
| 2 | 14.384 | 0.5385165 | 0.7348469 | −12.8808691 | 12.8825535 |
| 3 | 14.384 | 0.7348469 | 0.8888194 | −12.8825939 | 12.8852901 |
| 4 | 14.384 | 0.8888194 | 1.0198039 | −12.8843189 | 12.8880248 |
| 5 | 14.384 | 1.0198039 | 1.1357817 | −12.8860440 | 12.8907576 |
| 6 | 14.384 | 1.1357817 | 1.2409674 | −12.8877693 | 12.8934885 |
| 7 | 14.384 | 1.2409674 | 1.3379088 | −12.8894947 | 12.8962175 |
| 8 | 14.384 | 1.3379088 | 1.4282857 | −12.8912204 | 12.8989446 |
| 9 | 14.384 | 1.4282857 | 1.5132746 | −12.8929461 | 12.9016697 |
| 10 | 14.384 | 1.5132746 | 1.5937377 | −12.8946721 | 12.9043930 |
| 11 | 14.384 | 1.5937377 | 1.6703293 | −12.8963982 | 12.9071144 |
| 12 | 14.384 | 1.6703293 | 1.7435596 | −12.8981244 | 12.9098338 |
| 13 | 14.384 | 1.7435596 | 1.8138357 | −12.8998508 | 12.9125514 |

Figure 8:
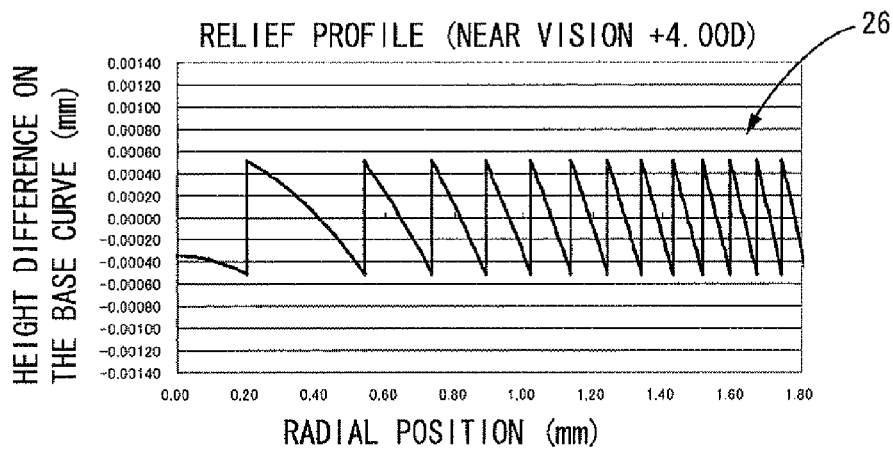
FIG. 8 is a relief profile of the relief for near vision, which composing the relief pattern.

As described above, curvature of the diffractive surface, geometric parameters such as the center position, and the relief profile of the relief 26 for near vision can be derived from the geometric relation. Table 1 shows geometric parameters of the relief 26 for near vision, and FIG. 8 shows the relief profile thereof.

Next, the relief pattern with the dioptric power at +2.00D is designed as the relief 28 for intermediate vision. The relief 28 for intermediate vision needs to be designed by designing the first order light with a different focal distance from that of the relief 26 for near vision while synchronizing it with the relief 26 for near vision determined by the above process.

First, a formula for calculating a zone radius of the relief 28 for intermediate vision is defined as follows:

$$\text{Zone radius} = \sqrt{(2M+A)\lambda(Nf)} \quad (5)$$

where M is a zone number, A is a zone constant, and N is a ratio of the focal distance of the relief for intermediate vision relative to that of the relief for near vision, which is expressed as:

(Focal distance of the relief for intermediate vision)/(Focal distance of the relief for near vision).

Then, in order to synchronize the relief 26 for near vision and relief 28 for intermediate vision, assuming that a given zone of the relief 26 for near vision coincides with a given zone of the relief 28 for intermediate vision, the following equation is derived from the above equations (3) and (5):

$$\sqrt{(2m+a)\lambda f} = \sqrt{(2M+A)\lambda(Nf)}$$

which is modified to obtain the following equation:

$$A = \{2(m-MN)+a\}/N \quad (6)$$

although A>0.

From the equation (6), the zone constant A is determined by the following equation, assuming that, for example, the zone No. 1 of the relief 26 for near vision coincides with the zone No. 0 of the relief 28 for intermediate vision:

$$A = \{2(1-0\times2)+0.32\}/2 = 1.16$$

The zone radius of the relief 28 for intermediate vision synchronized with the zone radius of the relief 26 for near vision is determined by the following equation:

$$\text{Zone radius} = \sqrt{(2M+1.16)\lambda(Nf)} \quad (7)$$

TABLE 2

Relief for intermediate vision

| Zone No. | Curvature radius of virtual base curve | Zone origin (X-axis) | Zone terminal (X-axis) | Curvature center of Zone (Y-axis) | Zone curvature radius |
|---|---|---|---|---|---|
| 0 | 14.384 | 0.0000000 | 0.5385165 | −13.5901614 | 13.5902427 |
| 1 | 14.384 | 0.5385165 | 0.8888194 | −13.5914234 | 13.5925192 |
| 2 | 14.384 | 0.8888194 | 1.1357817 | −13.5932909 | 13.5953967 |
| 3 | 14.384 | 1.1357817 | 1.3379088 | −13.5951586 | 13.5982706 |
| 4 | 14.384 | 1.3379088 | 1.5132746 | −13.5970264 | 13.6011407 |
| 5 | 14.384 | 1.5132746 | 1.6703293 | −13.5988945 | 13.6040072 |
| 6 | 14.384 | 1.6703293 | 1.8138357 | −13.6007627 | 13.6068698 |
| 7 | 14.384 | 1.8138357 | 1.9467922 | −13.6026312 | 13.6097288 |
| 8 | 14.384 | 1.9467922 | 2.0712315 | −13.6044998 | 13.6125840 |
| 9 | 14.384 | 2.0712315 | 2.1886069 | −13.6063686 | 13.6154355 |
| 10 | 14.384 | 2.1886069 | 2.3000000 | −13.6082376 | 13.6182832 |
| 11 | 14.384 | 2.3000000 | 2.4062419 | −13.6101067 | 13.6211272 |
| 12 | 14.384 | 2.4062419 | 2.5079872 | −13.6119761 | 13.6239675 |
| 13 | 14.384 | 2.5079872 | 2.6057628 | −13.6138457 | 13.6268040 |

Figure 9:
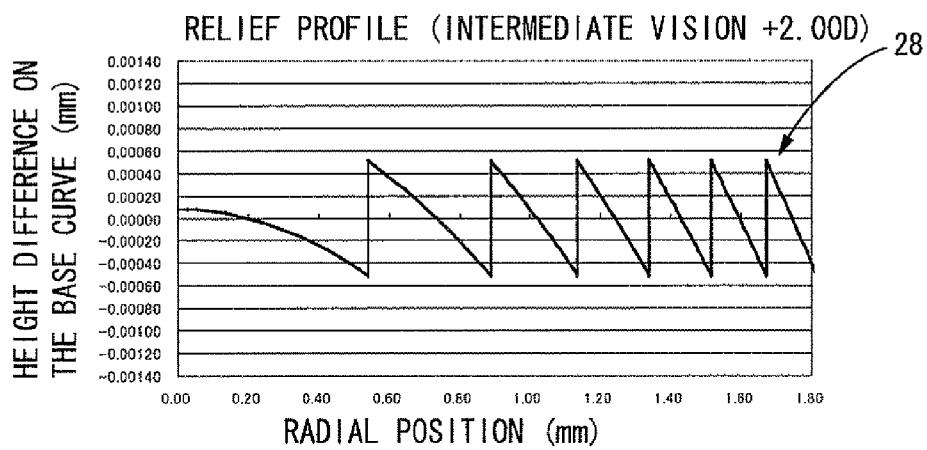
FIG. 9 is a relief profile of the relief for intermediate vision, which composing the relief pattern.

Besides, the height of the central relief and Y-axis value of the central apex can be determined in the same way as in the above relief 26 of near vision, and curvature of the diffractive surface, geometric parameters such as the center position, and the relief profile of the relief 28 for intermediate vision, which synchronizes with the relief 26 for near vision, is derived from the geometric relation. Table 2 shows geometric parameters of the relief 28 for intermediate vision, and FIG. 9 shows the relief profile thereof.

TABLE 3

Synchronized relief

| Zone No. | Curvature radius of virtual base curve | Zone origin (X-axis) | Zone terminal (X-axis) | Curvature center of Zone (Y-axis) | Zone curvature radius |
|---|---|---|---|---|---|
| 0 | 14.384 | 0.0000000 | 0.2000000 | −12.2385466 | 12.2382824 |
| 1 | 14.384 | 0.2000000 | 0.5385165 | −12.2391288 | 12.2398806 |
| 2 | 14.384 | 0.5385165 | 0.7348469 | −12.2416996 | 12.2444795 |
| 3 | 14.384 | 0.7348469 | 0.8888194 | −12.2434392 | 12.2472303 |
| 4 | 14.384 | 0.8888194 | 1.0198039 | −12.2465019 | 12.2523122 |
| 5 | 14.384 | 1.0198039 | 1.1357817 | −12.2482418 | 12.2550588 |
| 6 | 14.384 | 1.1357817 | 1.2409674 | −12.2513056 | 12.2601331 |
| 7 | 14.384 | 1.2409674 | 1.3379088 | −12.2530457 | 12.2628754 |
| 8 | 14.384 | 1.3379088 | 1.4282857 | −12.2561104 | 12.2679422 |
| 9 | 14.384 | 1.4282857 | 1.5132746 | −12.2578509 | 12.2706802 |
| 10 | 14.384 | 1.5132746 | 1.5937377 | −12.2609166 | 12.2757395 |
| 11 | 14.384 | 1.5937377 | 1.6703293 | −12.2626573 | 12.2784732 |
| 12 | 14.384 | 1.6703293 | 1.7435596 | −12.2657240 | 12.2835250 |
| 13 | 14.384 | 1.7435596 | 1.8138357 | −12.2674651 | 12.2862544 |

Figure 10:
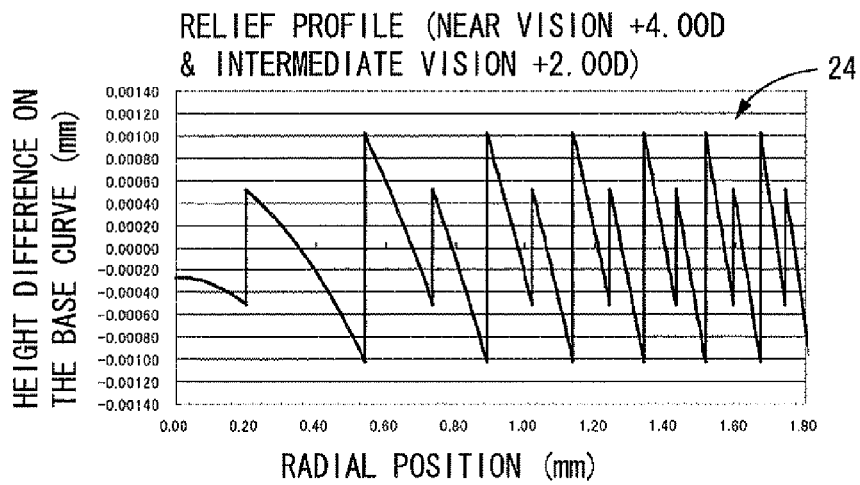
FIG. 10 is a relief profile of the relief pattern.

Subsequently, a relief profile of the relief pattern 24 having a synchronous structure where the relief 26 for near vision and relief 28 for intermediate vision are periodically overlapped by combining the relief profiles of the relief 26 for near vision and the relief 28 for intermediate vision is completed. Table 3 shows geometric parameters of the relief pattern 24 and FIG. 10 shows the relief profile thereof.

Then, according to the relief profile obtained, the relief pattern 24 is formed on the optical front surface 16. Formation of the relief pattern 24 on the optical front surface 16 is made not only by molding but also by machining and the like including laser processing, etching and cutting as appropriate. In this way, the intraocular lens 10 as the above embodiment is obtained.

An embodiment and a manufacturing method of this invention have been described thus far, but these are just examples, and this invention is not to be interpreted in a limited sense by any specific description of such embodiments. Several other aspects that can be preferably adopted in this invention will be shown below, but it should be understood that this invention is not limited to those aspects. In the descriptions below, details are omitted by applying the same reference numerals as those of the above embodiment to the same materials and parts as those thereof.

Figure 11:
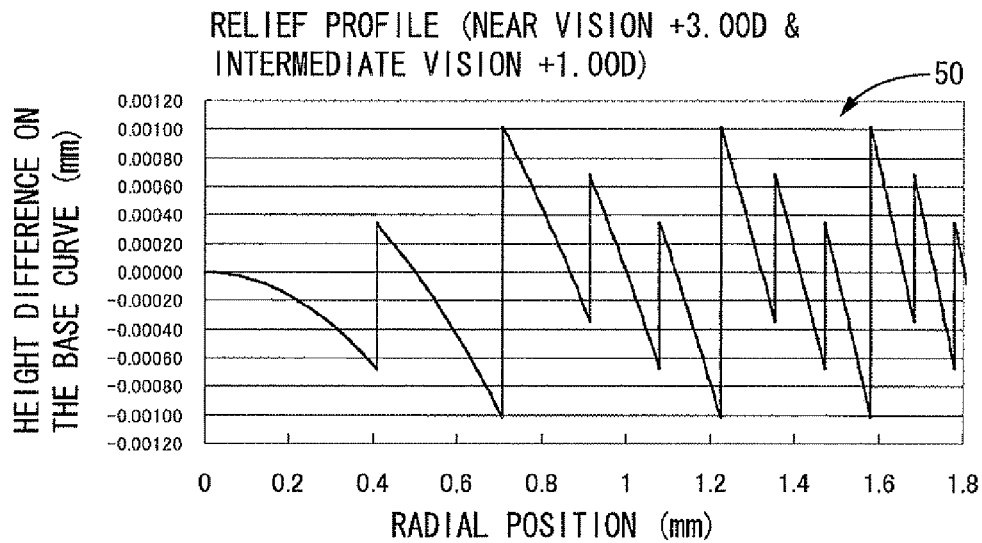
FIG. 11 is a relief profile of a relief pattern as a second embodiment of this invention.

First, FIG. 11 shows a relief profile of a relief pattern 50 as a second embodiment of this invention. In the present embodiment, a synchronous structure where two reliefs with the dioptric power at +3.0D for near vision and the other at +1.0D for intermediate vision are periodically overlapped. By the way, the relief profile of the present embodiment is the one obtained under the following settings:
Radius of the base curve of the optical front surface 16=8.000 mm
Dioptric power of the optical part 12=+25.0D
Refractive index of the lens material=1.500
Refractive index of the surrounding medium=1.336
Designed wavelength=500 nm
Zone constant of the relief for near vision 'a'=1

Meanwhile, the grating pitch is larger in the relief for intermediate vision than in the relief for near vision.

Especially in the present embodiment, two relief depths of the relief for near vision are provided per each zone of the relief for intermediate zone, and these three zones in total are formed, that is, in one out of three zone radii of the relief for near vision, the zone radius of the relief for intermediate vision is made equal to that of the relief for near vision. In each zone of the relief for intermediate vision composed of an overlap of reliefs for near vision, the height of the relief depth of the relief for near vision located between the relief depths of the relief for intermediate vision relative to the virtual base curve surface is made to vary gradually in the zone direction (left-right direction in FIG. 11), and in the present embodiment, the height is made to gradually decrease moving away from the center in the zone direction. Such relief pattern 50 can also be formed according to the same manufacturing method as the above first embodiment.

Figure 12:
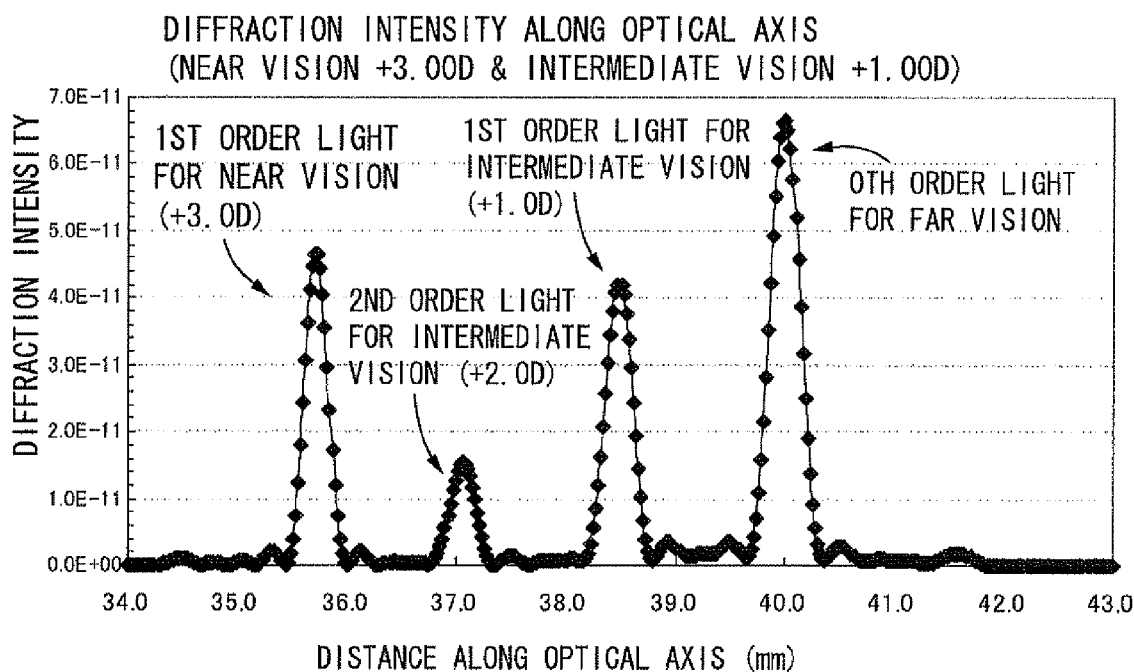
FIG. 12 is a graph showing a simulation result of diffraction intensity in the relief pattern.

Also, FIG. 12 shows a result of computer simulation of diffraction intensity along the optical axis obtained by the relief pattern 50 according to the present embodiment, just like the above first embodiment. As evident from FIG. 12, also in the present embodiment, it was confirmed that a peak of diffraction intensity is generated at the focus for intermediate vision of the first order diffracted light by the relief for intermediate vision between the focus for far vision of the 0th order light by the refractive surface and the focus for near vision of the first order diffracted light by the relief for near vision, and a peak is clearly generated in each of far, near and intermediate vision ranges.

In addition, especially in the present embodiment, the second order diffracted light of the relief for intermediate vision is generated. Thus, by changing the design parameters of the relief pattern 50, it is possible to generate multiple light beams for intermediate vision. Also, peak intensity and focal position of the diffracted light can be set in various aspects by means of, for example, further adding a relief that periodically overlaps with the relief pattern 50 having a synchronous structure.

Figure 13:
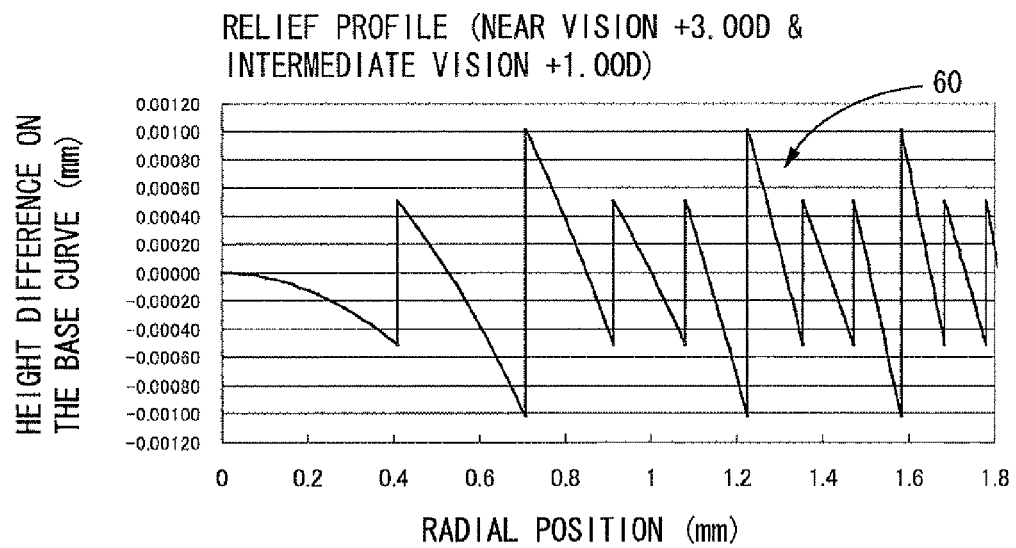
FIG. 13 is a relief profile of a relief pattern as a third embodiment of this invention.

Next, FIG. 13 shows a relief profile of a relief pattern 60 as a third embodiment of this invention. In the present embodiment, a synchronous structure where two reliefs with the dioptric power at +3.0D for near vision and at +1.0D for intermediate vision are periodically overlapped. Meanwhile, the grating pitch is larger in the relief for intermediate vision than in the relief for near vision.

In the present embodiment, two relief depths of the relief for near vision are provided per each zone of the relief for intermediate zone, and these three zones in total are formed, that is, in one out of three zone radii of the relief for near vision, the zone radius of the relief for intermediate vision is made equal to that of the relief for near vision. In each zone of the relief for intermediate vision composed of an overlap of reliefs for near vision, the height of the relief depth of the relief for near vision located between the relief depths of the relief for intermediate vision relative to the virtual base curve surface is kept approximately constant in the zone direction (left-right direction in FIG. 13).

Such relief pattern 60 can be manufactured by an easier method than the above first and second embodiments. In other words, a relief with a synchronous structure can be easily obtained by means of increasing the relief depth where the relief with a smaller grating pitch is overlapped with the one with a larger grating pitch based on the overlapping cycle of multiple reliefs on top of each other. For example, the dioptric power of the reliefs for near vision and intermediate vision in the present embodiment are the same as those of the above second embodiment, but as evident from the second embodiment (see FIG. 11), the relief for intermediate vision is synchronized with the relief for near vision once in every three times. Therefore, after designing the relief form for near vision according to the above manufacturing method, a relief pattern similar to that of the second embodiment can be obtained easily by means of increasing the relief depth of the obtained relief form for near vision once in every three times without exactly designing the relief form for intermediate vision like the above manufacturing method.

Figure 14:
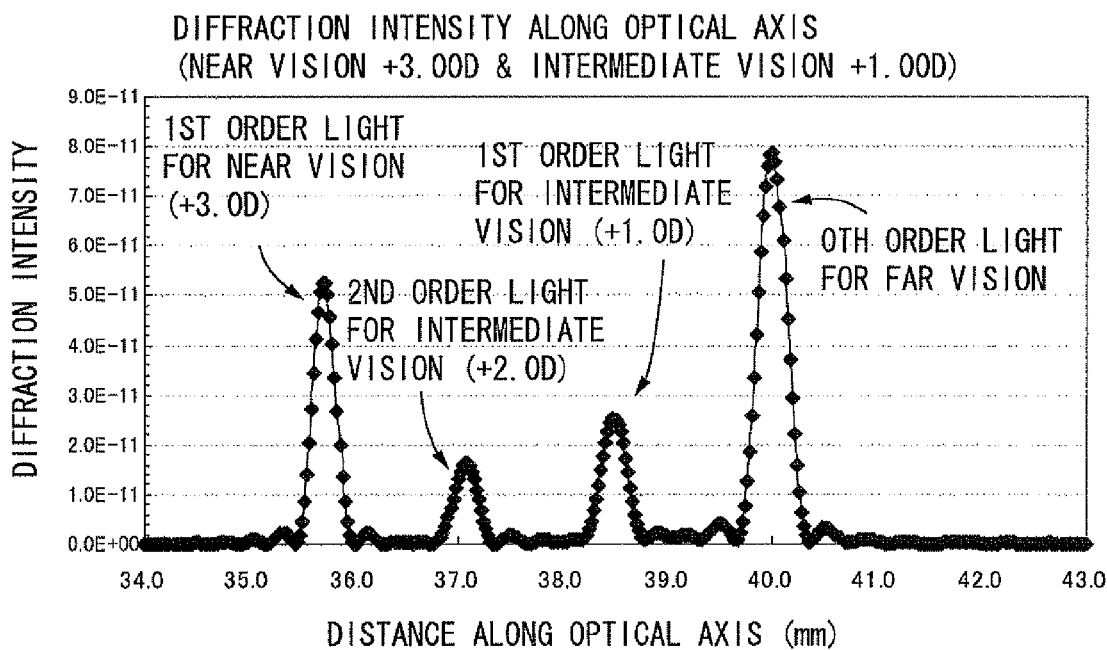
FIG. 14 is a graph showing a simulation result of diffraction intensity in the relief pattern.

Also, FIG. 14 shows a result of computer simulation of diffraction intensity along the optical axis obtained by the relief pattern 60 according to the present embodiment, as was done in the above first embodiment. As evident from FIG. 14, despite that diffraction intensity for intermediate vision drops slightly as opposed to the above second embodiment (see FIG. 12), it was confirmed that an effect similar to that of the above second embodiment can be achieved by generating a peak of diffraction intensity at the focus for intermediate vision by an easy manufacturing method according to the present embodiment.

Figure 15:
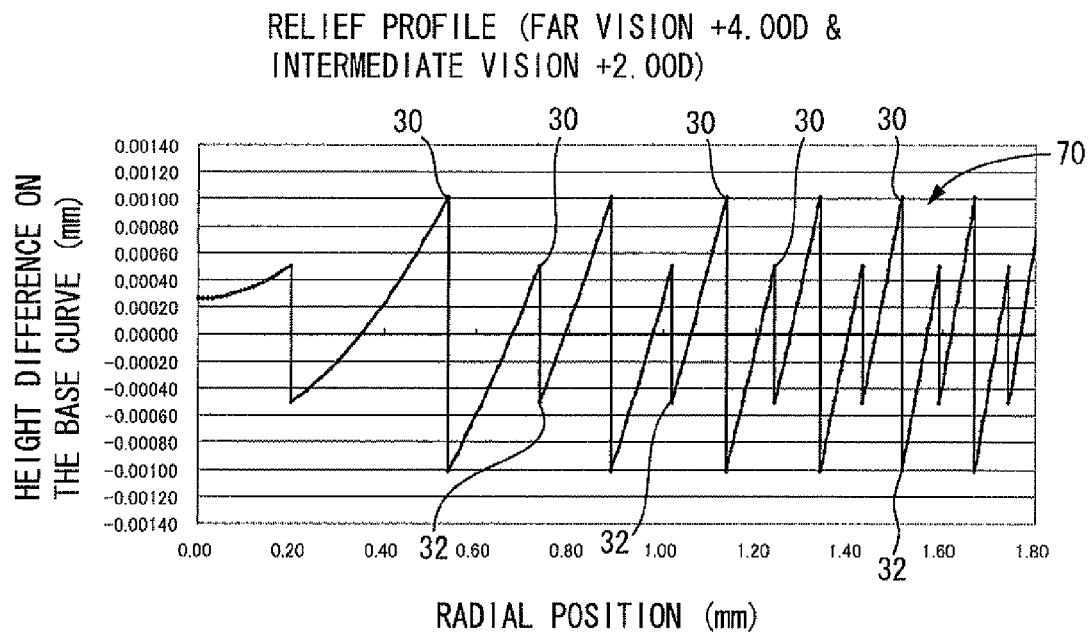
FIG. 15 is a relief profile of a relief pattern as a fourth embodiment of this invention.

Next, FIG. 15 shows a relief pattern 70 in profile as a fourth embodiment of this invention. In the present embodiment, a synchronous structure where two reliefs with the dioptric power at +4.0D for far vision and at +2.0D for intermediate vision are periodically overlapped. Meanwhile, the grating pitch is larger in the relief for intermediate vision than in the relief for far vision.

As evident from FIG. 15, the relief pattern 70 of the present embodiment has its depth with the positive and negative reversed from that of relief pattern 24 (see FIG. 10) in the above first embodiment, and the ridge line 30 is positioned closer to the center than the valley line 32 in each zone. According to the present embodiment, the 0th order light of the refractive surface is set to focus for near vision and the negative first order light of the relief for far vision is set to focus for far vision, while the negative first order light of the relief for intermediate vision is set to focus for intermediate vision. And as described above, the first order diffracted light of this invention is to be interpreted as first order light with an absolute value including the negative first order light.

Figure 16:
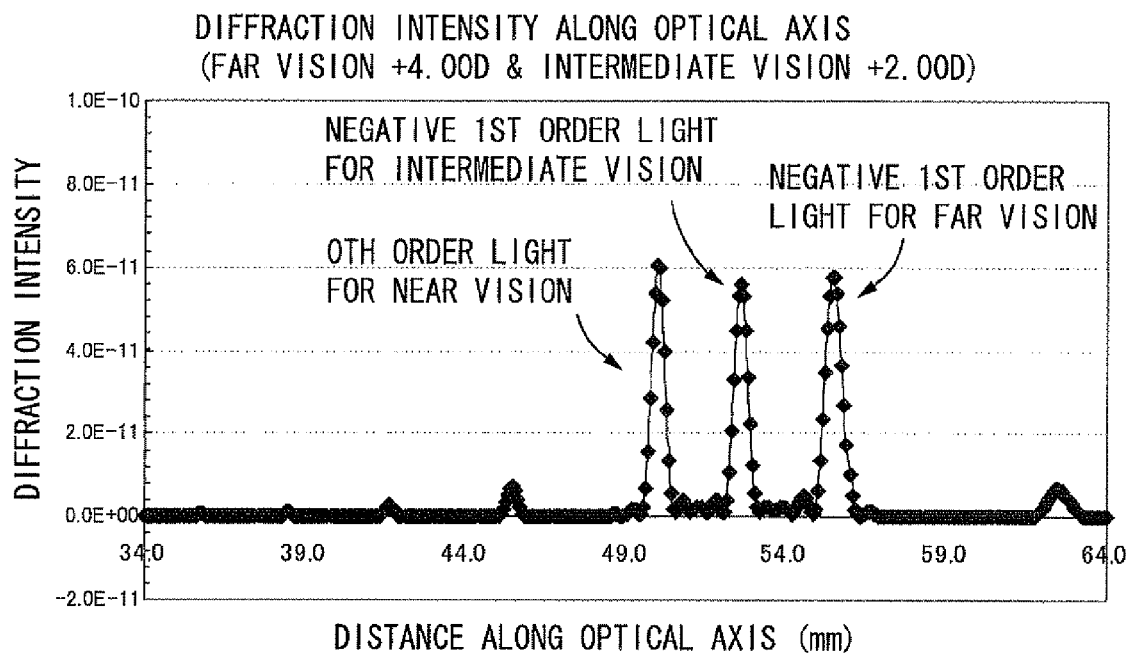
FIG. 16 is a graph showing a simulation result of diffraction intensity in the relief pattern.

Also, FIG. 16 shows a computer simulation result of diffraction intensity along the optical axis obtained by the relief pattern 60 according to the present embodiment, as was done in the above first embodiment. As evident from FIG. 16, a peak of diffraction intensity at the focus for far vision by the negative first order light of the relief for far vision is generated in addition to that at the focus for near vision by the 0th order light of the refractive surface, according to the present embodiment, while a peak of diffraction intensity at the focus for intermediate vision by the negative first order light of the relief for intermediate vision is generated between these foci for near vision and far vision. Also, it was confirmed that a peak can be clearly generated in each of far, near and intermediate vision ranges in the present embodiment, too.

Figure 17:
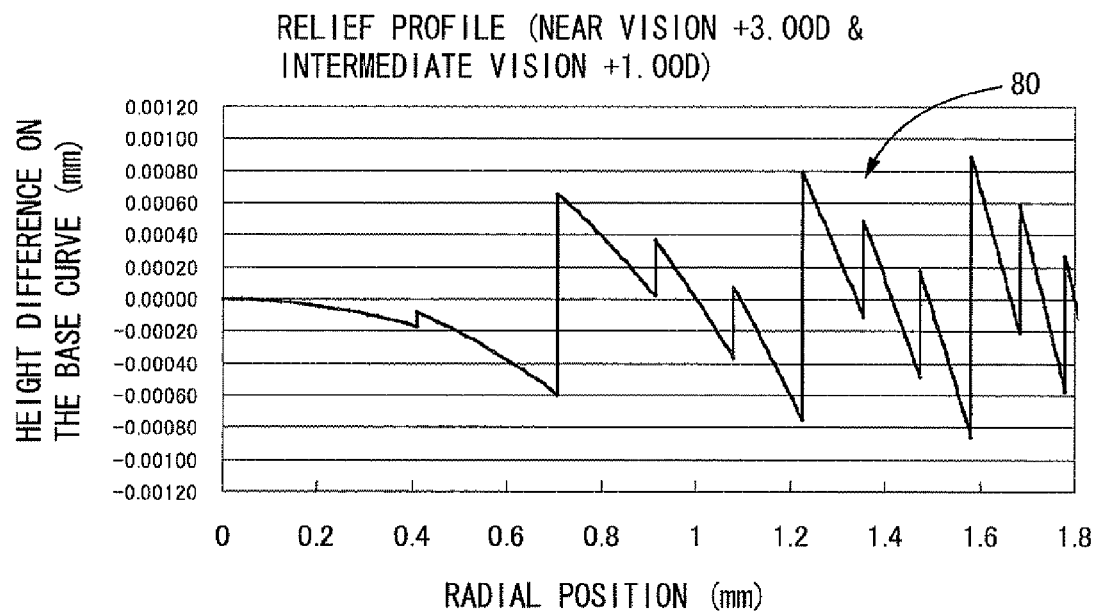
FIG. 17 is a relief profile of a relief pattern as a fifth embodiment of this invention.

Next, FIG. 17 shows a relief pattern 80 in profile as a fifth embodiment of this invention. In the present embodiment, a synchronous structure where two reliefs with the dioptric power at +3.0D for near vision and at +1 MD for intermediate vision are periodically overlapped. Meanwhile, the grating pitch is larger in the relief for intermediate vision than in the relief for near vision.

The relief pattern 80 of the present embodiment is in a similar form to that of the relief pattern 50 (see FIG. 11) as the above second embodiment, and especially in the present embodiment, only the relief component for near vision is made to increase outward from the center at zero as compared to the relief pattern 50 as the above second embodiment. This makes it possible to reduce diffractive intensity for near vision.

Figure 18:
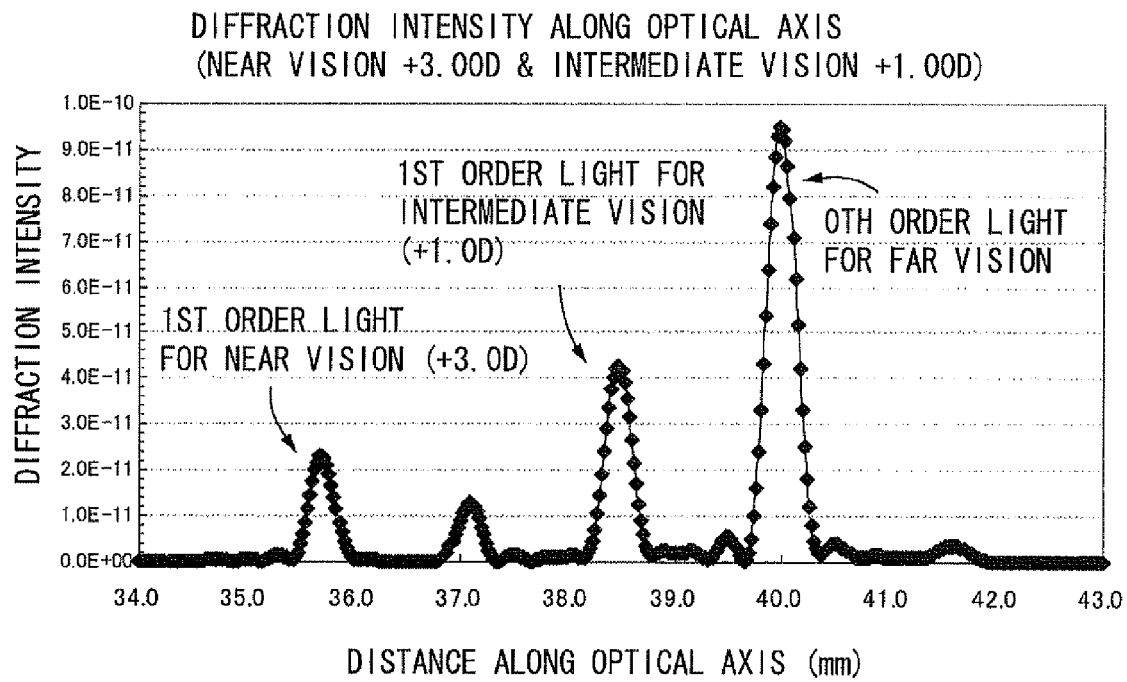
FIG. 18 is a graph showing a simulation result of diffraction intensity in the relief pattern.

Also, FIG. 18 shows a computer simulation result of diffractive intensity along the optical axis obtained by the relief pattern 80 according to the present invention, as was done in the above first embodiment. As evident from FIG. 18, it is confirmed that a peak of diffraction intensity at the focus for near vision can be reduced, according to the present embodiment, as compared to the above second embodiment (see FIG. 12).

Also, in each of the above embodiments, a diffraction grating with a synchronous structure where multiple reliefs are periodically overlapped was formed almost all over the optical front surface 16 of the optical part 12, but it will suffice for such a diffraction grating to be formed in at least a part of the area in the radial direction of the lens, for example, only in the middle of the optical front surface 16 in the radial direction. Consequently, only a single relief can be formed or the like in the other part of the area. For example, in case of the relief pattern 24 formed on the intraocular lens 10 as the above first embodiment, it is of course possible to form the diffraction grating with a synchronous structure on the optical rear surface 18.

Figure 19:
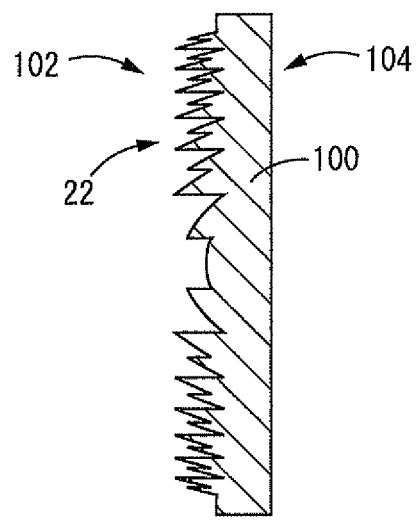
FIG. 19 is a cross-section diagram showing an optical part of an intraocular lens as a different aspect of this invention.
Figure 20:
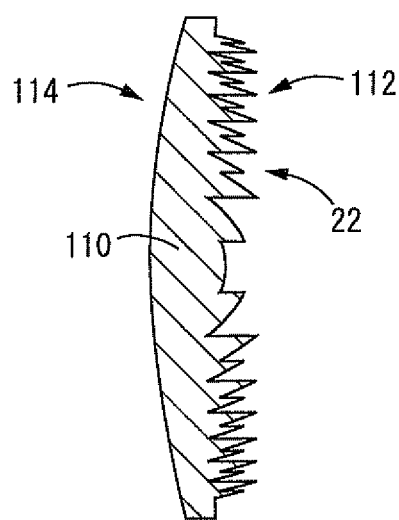
FIG. 20 is a cross-section diagram showing an optical part of an intraocular lens as a further different aspect of this invention.

Additionally, the lens surface where the diffraction grating with a synchronous structure is formed is not limited to refractive surfaces. For example, as shown diagrammatically in FIG. 19, the diffraction grating 22 can be formed on a plane 102, one of the two planes 102 and 104 of an optical part 100 of an intraocular lens as a different aspect of this invention, or as shown diagrammatically in FIG. 20, the diffraction grating 22 can even be formed on a plane 112 of an optical part 110 of an intraocular lens as a further different aspect of this invention where one surface is the flat plane 112 and the other is a curved plane 114 as refractive surface.

Furthermore, for the purpose of reducing aberration, it is possible to form a diffraction grating according to this invention, for example, on a surface of a laminate of two materials with different dispersion, as described in JP-A-2001-42112.

Figure 21:
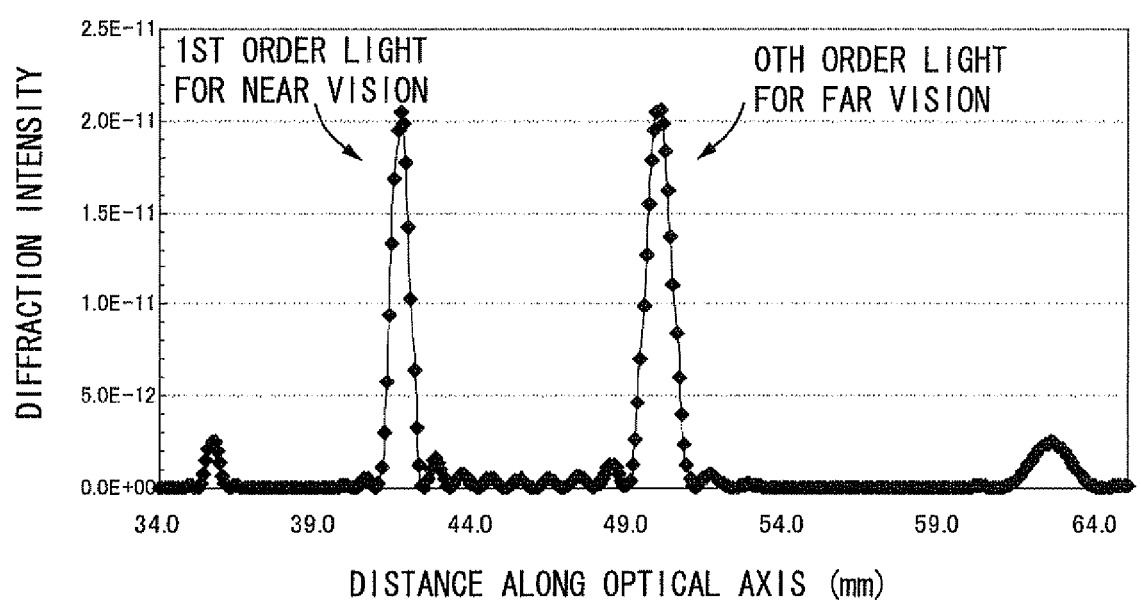
FIG. 21 is a graph showing a simulation result of diffraction intensity of a relief pattern according to a conventional structure.

Also, as the comparative example 1 as compared to the working example according to the above first embodiment (see FIG. 6), a computer simulation has been performed of diffraction intensity obtained by a relief pattern of a bifocal lens according to the conventional structure. The relief pattern of the comparative example 1 was set at a dioptric power of +4.00D for near vision. A result of such simulation is shown in FIG. 21. As is publicly known, in the comparative example 1 according to the conventional structure, it is confirmed that only two peaks can be generated, one by the 0th order light of the refractive surface and the other by the first order diffracted light of the relief for near vision, unlike the working example.

Figure 22A:
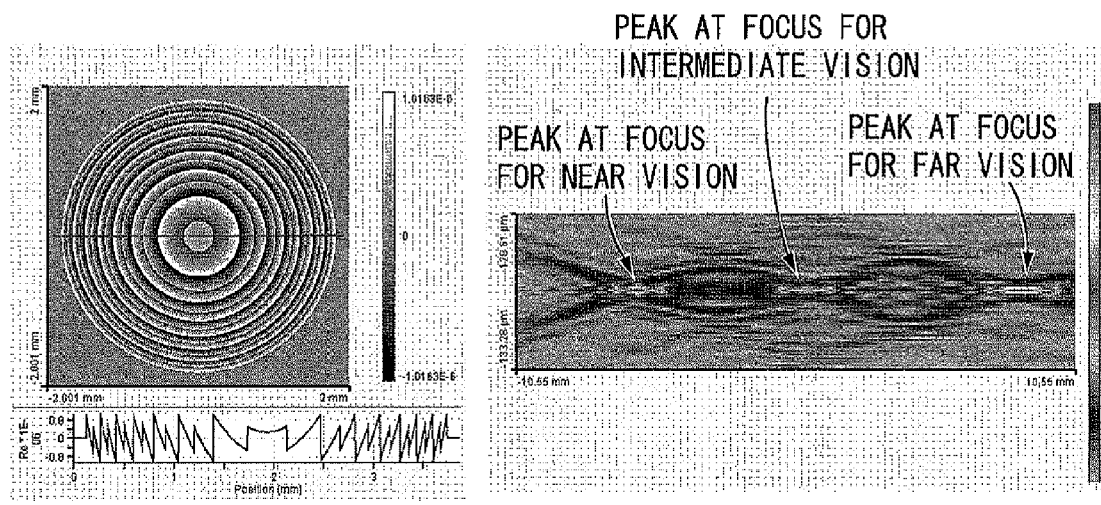
FIGS. 22A and 22B show simulation results of diffraction intensity of relief patterns with a structure according to this invention and a structure according to the prior art.
Figure 22B:
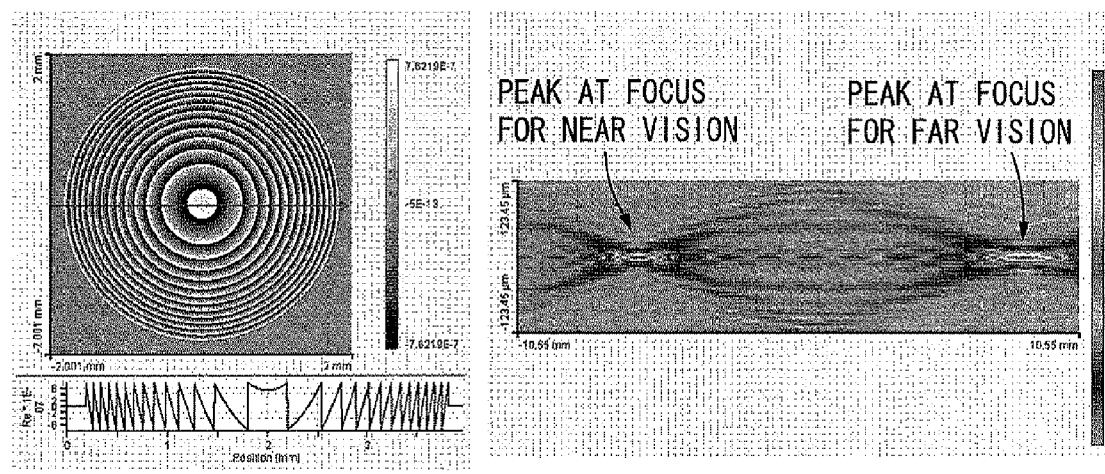

In addition, in order to enhance the reliability of the simulation result, generation of peaks of diffraction intensity was verified for the relief pattern according to the working example and the relief pattern according to the comparative example 1 using an wave-optical design and analysis software (VirtualLab, a brand name of LightTrans). Such verifications are shown in FIG. 22A for the working example and in FIG. 22B for the comparative example 1. As evident from FIGS. 22A and 22B, it was also confirmed in this simulation, according to the working example with a structure following this invention, that an intensive peak of diffraction intensity at the focus for intermediate vision is generated between the foci for far vision and near vision, unlike in the conventional structure.

Figure 23:
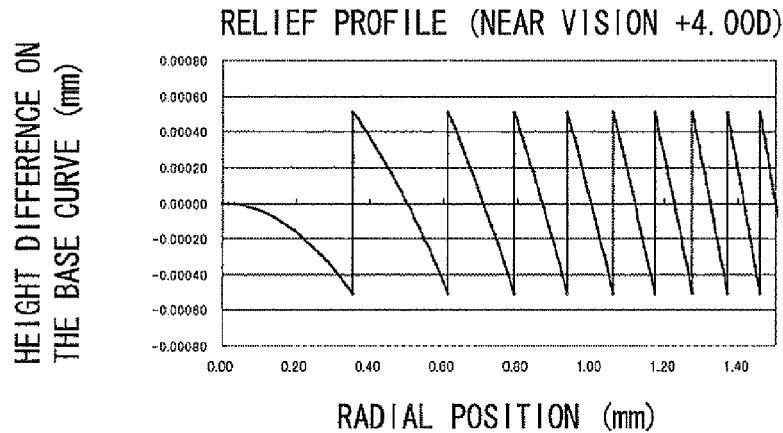
FIG. 23 is a relief profile of a relief for near vision, which composing a relief pattern as a comparative example 2.
Figure 24:
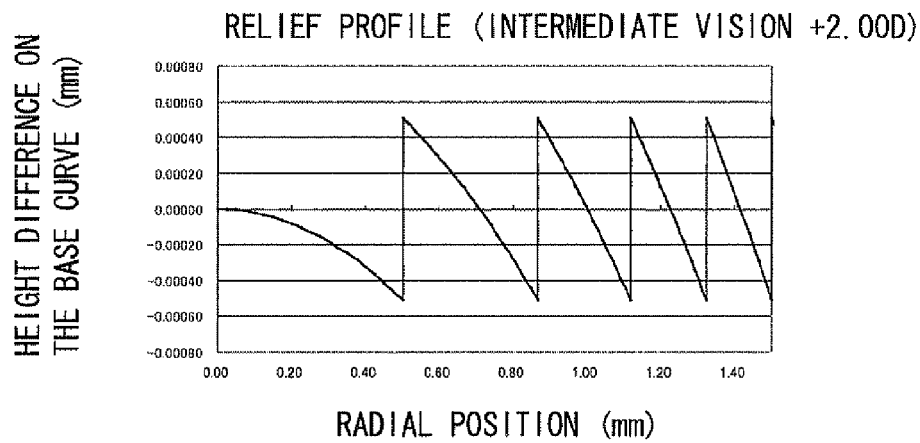
FIG. 24 is a relief profile of a relief for intermediate vision, which composing the relief pattern as the comparative example 2.
Figure 25:
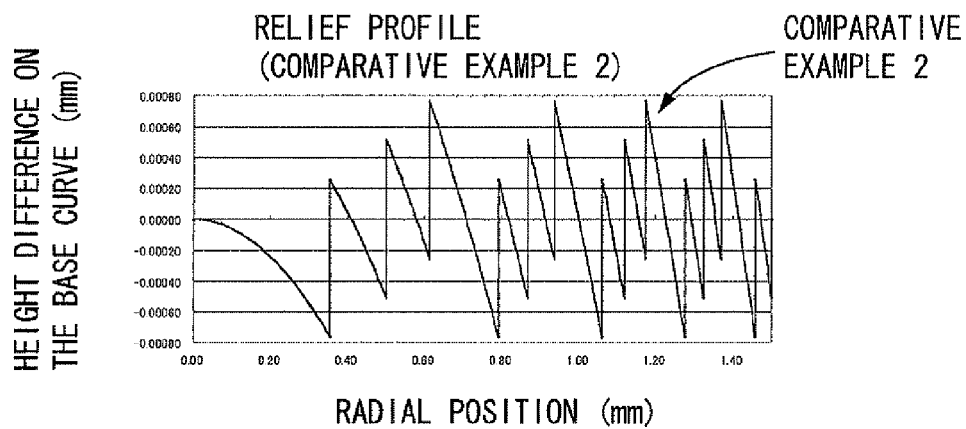
FIG. 25 is a relief profile showing the relief pattern as the comparative example 2.
Figure 26:
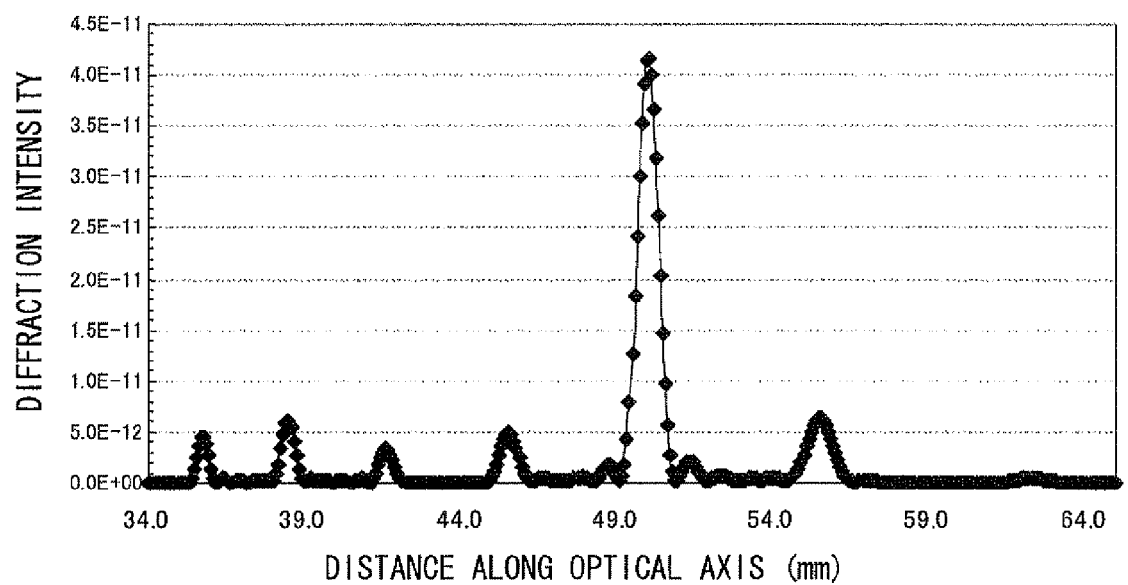
FIG. 26 is a graph showing a simulation result of diffraction intensity of the relief pattern.

Also, as the comparative example 2, an intraocular lens having a relief pattern with an asynchronous structure where the reliefs for near vision and intermediate vision are simply overlapped with no synchronization prepared. In this comparative example 2, an intraocular lens in a biconvex form was set to have its dioptric power at +20.0D, refractive index of the lens material at 1.500, refractive index of the surrounding medium at 1.336, and design wavelength at 500 nm, while the relief for near vision with the dioptric power at +4.00D and the relief for intermediate vision with the dioptric power at +2.00D, with each zone constant set at 1, were overlapped in an asynchronous form to set a relief pattern, which was formed on the optical front surface. FIGS. 23 and 24 show the relief profiles of the relief for near vision and intermediate vision, respectively. FIG. 25 shows, as the comparative example 2, a relief profile which is an overlap of these reliefs for near vision and intermediate vision with no synchronization, while FIG. 26 shows a simulation result of diffraction intensity obtained by the relief pattern of said comparative example 2. As evident from FIG. 26, in the comparative example 2 which is a simple overlap of multiple relief patterns, it was confirmed that no obvious generation of peaks was detected in any of the 0th order light by the refractive surface, the first order diffractive light by the relief for near vision, or the first order diffractive light by the relief for intermediate vision, causing to generate peaks of unintended order of light. This revealed the usefulness of this invention wherein a synchronous structure is set where multiple reliefs are periodically overlapped.

KEYS TO SYMBOLS

10: Intraocular lens, 12: Optical part, 16: Optical front surface, 20: Lens center axis, 22: Diffraction grating, 24: Relief pattern, 26: Relief for near vision, 28: Relief for intermediate vision.

The invention claimed is:

1. An aphakic intraocular lens adapted to be set in place in a lens capsule, and provided with a diffraction grating having a relief pattern extending concentrically on a lens surface, comprising:

a synchronous structure where various types of reliefs including at least two reliefs whose first order diffracted lights give respective focal distances different from one another are set to overlap with each other in at least a part of an area in a radial direction of the lens, and with respect to every grating pitches of one relief having a maximum grating pitch among the reliefs set up in overlap, grating pitches of another relief being overlapped periodically.

2. The aphakic intraocular lens according to claim 1, wherein a focal distance different from that of any first order diffracted light generated by the various types of reliefs is set for a 0th order light by a refractive surface of the lens.

3. The aphakic intraocular lens according to claim 2, wherein the lens surface formed with the relief pattern is the refractive surface.

4. The aphakic intraocular lens according to claim 1, wherein each relief depth of the relief having the maximum grating pitch, which is obtained by overlapping the various types of reliefs, is made constant in a zone direction.

5. The aphakic intraocular lens according to claim 4, wherein in each zone in the relief having the maximum grating pitch, another type of relief with at least two relief depths is formed in the area in the radial direction of the lens where the various types of reliefs set up in overlap, and dimensions of the at least two relief depths relative to a virtual base curve surface vary gradually in the zone direction.

6. The aphakic intraocular lens according to claim 4, wherein in each zone in the relief having the maximum grating pitch, another type of relief with at least two relief depths is formed in the area in the radial direction of the lens where the various types of reliefs set up in overlap, and dimensions of the at least two relief depths relative to a virtual base curve surface are set constant in the zone direction.

7. The aphakic intraocular lens according to claim 1, wherein each of the various types of reliefs has a ridge line extending circumferentially with a cross-section formed with an acute vertex angle and a valley line extending circumferentially with a cross-section formed with an acute included angle.

8. The aphakic intraocular lens according to claim 1, wherein a 0th order light by a refractive surface of the lens is set to a focus for far vision, the first order diffracted light by one type of the relief is set to a focus for near vision, and the first order diffracted light by another type of the relief is set to a focus for intermediate vision.

9. The aphakic intraocular lens according to claim 1, wherein a 0th order light by a refractive surface of the lens is set to a focus for near vision, the first order diffracted light by one type of the relief is set to a focus for far vision, and the first order diffracted light by another type of the relief is set to a focus for intermediate vision.

10. The aphakic intraocular lens according to claim 1, wherein the various types of reliefs are arranged to satisfy a following equation:

$$A=(2(m-NM)+a)/N$$

where A is a zone constant of the one relief, 'a' is a zone constant of the other relief, M is a zone number of the one relief, m is a zone number of the other relief, and N is a ratio of a focal distance of the one relief relative to that of the other relief, which is expressed as:

(focal distance of the one relief)/(focal distance of the other relief).

11. The aphakic intraocular lens according to claim 1, wherein the various types of reliefs are arranged to satisfy a following equation:

$$D \leq \lambda/(N_{lens}-N_{med})$$

where D is a dimension of a relief depth, $\lambda$ is a design wavelength, $N_{lens}$ is a refractive index of an optical material, and $N_{med}$ is a refractive index of a surrounding medium.

* * * * *